United States Patent
Dhurandhar

(10) Patent No.: US 8,951,980 B2
(45) Date of Patent: Feb. 10, 2015

(54) ADENOVIRUS AD36 E4 ORF1 PROTEIN FOR PREVENTION AND TREATMENT OF NON-ALCOHOLIC FATTY LIVER DISEASE

(75) Inventor: Nikhil V. Dhurandhar, Baton Rogue, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 396 days.

(21) Appl. No.: 13/178,986

(22) Filed: Jul. 8, 2011

(65) Prior Publication Data

US 2012/0027845 A1    Feb. 2, 2012

Related U.S. Application Data

(60) Provisional application No. 61/362,443, filed on Jul. 8, 2010.

(51) Int. Cl.
*A61K 48/00* (2006.01)
*A61K 38/16* (2006.01)

(52) U.S. Cl.
CPC ........... *A61K 38/162* (2013.01); *A61K 48/00* (2013.01); *C12N 2710/10333* (2013.01)
USPC ....................................... 514/44 R

(58) Field of Classification Search
None
See application file for complete search history.

(56) References Cited

U.S. PATENT DOCUMENTS 8,008,436 B2 *   8/2011   Dhurandhar et al. ......... 530/350

FOREIGN PATENT DOCUMENTS

WO    WO2007/064836    6/2007

OTHER PUBLICATIONS

Atkinson, "Human Adenovirus-36 and Non-Alcoholic Fatty Liver Disease," Liver International, 30:164-165 (2010).
Dhurandhar et al., "E4orf1: A Novel Ligand that Improves Glucose Disposal in Cell Culture," PLoS One, 6:1-12 (2011).
International Search Report from corresponding PCT Application No. PCT/US2011/043338 dated Nov. 25, 2011.
Krishnapuram et al., "Template to Improve Glycemic Control Without Reducing Adiposity or Dietary Fat," Am. J. Physiol. Endocrinol. Metab., 300:E779-E789 (2011).
Trovato et al., "Ad36 Adipogenic Adenovirus in Human Non-Alcoholic Fatty Liver Disease," Liver International, 30:184-190 (2009).
Trovato et al., "Adenovirus-36 Seropositivity Enhances Effects of Nutritional Intervention on Obesity, Bright Liver, and Insulin Resistance," Dig. Dis. Sci., 10 pages (2011).
"Non-alcoholic fatty liver disease," Chao-Chuen Chi, pp. 4-5, and 64-65, Military Medical Science Press, Sep. 1, 2009 (English translation).

* cited by examiner

*Primary Examiner* — Michael Burkhart
(74) *Attorney, Agent, or Firm* — McDermott Will & Emery LLP

(57) ABSTRACT

This invention generally relates to methods for treating or preventing the symptoms of non-alcoholic fatty liver disease, methods for reducing excessive fat from the liver, methods of improving glycemic control, and methods for treating or preventing liver dysfunction, that comprise administering a therapeutically effective amount of Adenovirus 36 E4orf1 protein or functional variant thereof.

26 Claims, 15 Drawing Sheets

ADENOVIRUS AD36 E4 ORF1 PROTEIN FOR PREVENTION AND TREATMENT OF NON-ALCOHOLIC FATTY LIVER DISEASE

GOVERNMENT FUNDING

The development of this invention was partially funded by the Government under a grant from the National Institutes of Health, grant no. R01 DK066164. The Government has certain rights to this invention.

CROSS-REFERENCES TO RELATED APPLICATIONS

The present application claims the benefit of U.S. Provisional patent application Ser. No. 61/362,443, entitled "Adenovirus Ad36 E4orf1 Protein for Prevention and Treatment of Non-alcoholic Fatty Liver Disease," filed on Jul. 8, 2010, which is hereby incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Sep. 28, 2011, is named 07117631.txt and is 5,155 bytes in size.

BACKGROUND

The liver has a predominate role in fat metabolism and normally accumulates lipids (fat), but only to "normal levels." Excessive lipid accumulation in hepatocytes results in hepatic steatosis, which is metabolically harmful and can result from a variety of liver dysfunctions, such as decreased beta-oxidation or decreased secretion of lipoproteins. Another of the many functions of the liver is to release glucose into the circulation. In healthy individuals, liver cells release glucose regularly to regulate blood glucose levels. In contrast, in individuals with diabetes, liver cells release glucose uncontrollably, which increases blood glucose levels. Therefore, reducing glucose release from liver cells (hepatocytes) can be very effective in controlling diabetes.

Excessive lipid accumulation in the liver may contribute to insulin resistance, and thus poor glycemic control. Adiponectin, a protein secreted by fat tissue (adipose tissue) improves insulin sensitivity in many ways. Adiponectin acts via adiponectin receptors AdipoR1 and AdipoR2 to activate AMPK and PPARα pathways (32), to decrease systemic and hepatic insulin resistance, and to attenuate liver inflammation and fibrosis (32). It is a strong determinant of hepatic lipid content, as indicated by mice models of adiponectin KO or overexpression (14, 33). Adiponectin lowers hepatic steatosis by the up-regulation of AMPK-mediated hepatic lipid oxidation (34).

Non-alcoholic fatty liver disease (NAFLD) affects up to 20% of adults in the U.S., and includes the excessive accumulation of fat in the liver (hepatic steatosis). It is often associated with obesity and insulin resistance (1, 2). The prevalence of NAFLD is about 70-80% in adults with type 2 diabetes or obesity (3-5), 3-10%, in all children, and up to 40-70% in obese children (4). NAFLD is associated with greater overall and liver-related mortality (6, 7). In addition to steatosis, inflammation and fibrosis can develop and NAFLD may progress to non-alcoholic steato-hepatitis (NASH), cirrhosis, liver failure and hepatocellular carcinoma. While steatosis is potentially reversible, once it progresses to NASH, there are no established treatments, and the few available medications show limited success (8, 9). Therefore, the timely prevention and/or treatment of hepatic steatosis is critical. However, even for NAFLD, drug treatment has marginal success (10), and reducing dietary fat intake and obesity are the mainstay of treatment (11). Despite the obvious health benefits, compliance with lifestyle changes to achieve sustained improvements in diet or obesity has proved challenging for the general population.

While excess adiposity or a high fat (HF)-diet are risk factors for NAFLD, Adenovirus 36 (Ad36) attenuates hepatic steatosis in mice despite a continued HF-diet and without a reduction in visceral or subcutaneous adiposity. Ad36 appears to qualitatively engineer existing adipose tissue to attenuate HF-diet induced hepatic steatosis. This change in metabolic quality of adipose tissue by Ad36 includes greater uptake and reduced release of fatty acids and greater adiponectin secretion (12, 13). This unique capability of Ad36 offers a remarkable model to creatively negate the ill effects of excess adiposity or excess dietary fat intake, without the need to reduce it. Thiazolidinediones (TZDs) class of drugs can also improve metabolic quality of adipose tissue, up-regulate adiponectin, and improve hepatic steatosis (14-16). Serious side effects of TZDs have been reported (17-19).

Ad36 does not cause morbidity or unintended mortality in animals. In addition, Ad36 appears to have distinct advantages over the action of the TZDs, particularly in the presence of a HF-diet. Unlike the TZDs Ad36 does not increase adiposity in HF-fed mice (20, 21). In the presence of a HF-diet, TZDs can improve glycemic control, but they concurrently promote lipid storage in various organs, including the liver (20, 22, 23). This limits the scope of TZDs, if fat intake is not reduced. Due to its dietary-fat and adiposity-independent effects, potential action of Ad36 on multiple metabolic pathways may offer a novel anti-steatosis approach that is clinically more attractive, and, therefore, potentially more effective.

Harnessing certain properties of viruses for beneficial purposes has been creatively used for several years, including the use of bactericidal properties of a bacteriophage virus (27), the oncolytic ability of a mutant adenovirus (28), or the use of Herpes simplex virus and several other viruses for the treatment of cancers (29), alone, or with various synergistic drugs (30, 31).

Therefore, agents to lower hepatic steatosis independent of adiposity or dietary fat intake would be extremely attractive and of practical benefit.

SUMMARY OF THE INVENTION

The invention relates to the discovery that Ad36 infection is associated with decreased incidence of liver pathology and dysfunction, and that the Ad36 E4orf1 protein can be used to alter gene expression and biochemical pathways that result in improved liver function.

The invention generally relates to methods of treating or preventing the symptoms of non-alcoholic fatty liver disease in an individual. In some aspects, the method comprises administering to the individual a therapeutically effective amount of Adenovirus-36 E4orf1 protein, wherein the individual's symptoms improve following the administration.

The invention also relates to methods of reducing excessive fat in the liver in an individual. In some aspects, the method comprises administering to the individual a therapeutically effective amount of Adenovirus-36 E4orf1 protein, wherein the fat in the liver is lowered following the administration.

The invention also relates to methods of improving glycemic control in an individual. In some aspects, the method comprises administering to the individual a therapeutically effective amount of Ad36 E4orf1 protein, wherein insulin sensitivity is increased following the administration.

The invention also relates to methods of treating or preventing liver dysfunction, characterized by fatty liver and/or insulin resistance. In some aspects, the method comprises administering to the individual a therapeutically effective amount of Ad36 E4orf1 protein, wherein liver fat accumulation is improved following the administration. The improvement of liver fat accumulation can be characterized by increased lipid oxidation or increased transport of lipid from the liver.

The invention also relates to methods of reducing or preventing NASH. In some aspects, the method comprises administering to the individual a therapeutically effective amount of Ad36 E4orf1 protein, wherein hyperglycemia resulting from hepatic dysfunction is reduced.

The amino acid sequence of the Adenovirus-36 E4orf1 protein can be SEQ ID NO:2 or functional variants thereof. The nucleic acid sequence of the Adenovirus-36 E4orf1 can comprise SEQ ID NO:1 or functional variants thereof. The individual can be a human.

The Adenovirus-36 E4orf1 protein can be administered to the individual by introducing into the individual a nucleic acid molecule encoding the Adenovirus-36 E4orf1 protein, in a manner permitting expression of the Adenovirus-36 E4orf1 protein. The nucleic acid sequence can be introduced by using any suitable method. Many suitable methods are conventional in the art, such as electroporation, DEAF Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, nanoparticle delivery, viral vectors, and naked DNA transfer.

BRIEF DESCRIPTION OF THE DRAWINGS

FIG. 7 shows Western blots using adipose tissue proteins from HF-fed mice killed in free fed state 20 wk post infection. (3 mice/group).

DETAILED DESCRIPTION

Overview

Figure 1:
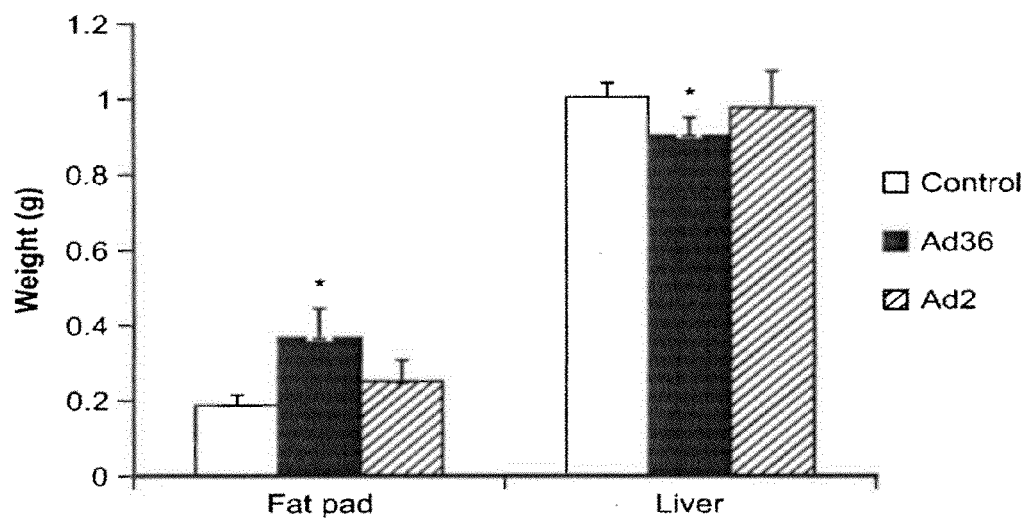
FIG. 1 is a graph showing weights of retroperitoneal fat pad and liver in chow-fed mice.

The invention relates to the discovery that Ad36 infection is associated with decreased incidence of liver pathology and dysfunction, and that the Ad36 E4orf1 protein can be used to alter gene expression and biochemical pathways that result in improved liver function. Based on these discoveries, non-alcoholic fatty liver disease (NAFLD) can be treated or even prevented by administering Ad36 or isolated or recombinant Ad36 E4orf1 protein to an individual. It is well known in the art that NAFLD frequently progresses to NASH therefore by treating or reducing the pathological processes of NAFLD, the progression to NASH can be reduced or prevented. Accordingly, the invention also includes a method for reducing or preventing NASH. While many viruses cause serious liver injury (25, 26), Ad36 and Ad36 E4orf1 surprisingly protect the liver by favorably modulating multiple metabolic pathways, thereby having a beneficial effect on hepatic steatosis and liver function.

As used herein, "glycemic control" refers to the ability of the body to keep glucose levels within the normal range. Glycemic control is improved when insulin sensitivity increases. Insulin resistance has the opposite effect on glycemic control.

As used herein, "glucose uptake" refers to the amount of glucose a cell will take in from its surroundings. Generally a higher glucose uptake by muscle cells or fat cells (adipocytes and preadipocytes), is beneficial, as it clears the glucose from circulation and improves hyperglycemia (higher than normal glucose in the blood).

A link between natural Ad36 infections of humans and better glycemic control and lower hepatic lipid was discovered. This link was further investigated in animal models, and the results confirmed that Ad36 infection unexpectedly lowered hepatic lipid levels and improved glycemic control. Further investigation revealed that the Ad36 effect is mediated by the Ad36 E4orf1 protein. As described herein, the results of the studies conducted demonstrate that the Ad36 E4orf1 protein increased fat oxidation in the liver, increased transport of fat from the liver and reduced glucose release from the liver. Thus, the inventors have discovered that the viral protein, Ad36 E4orf1, is responsible for the protective effect of Ad36 on NAFLD, and beneficial effects on liver function and glycemic control. The Ad36 E4orf1 structure and certain metabolic functions are described in International application no. PCT/US2006/045919, published as International publication no. WO 2007/064836 on Jun. 7, 2007.

As shown herein, E4orf1 protein of Ad36 is the mediator of protective effect of the Ad36 virus on hepatic steatosis. Ad36 infected mice continue to express E4orf1 gene in their livers, even 5 months post infection. These livers show significantly lower lipid accumulation, and greater expression of genes that promote lipid oxidation and lipid export. In addition, Ad36 E4orf1 up-regulates adiponectin, and transfection of HepG2 cells (hepatocyte cell line) with Ad36 E4orf1 down regulates Glut2 abundance, and glucose release Without wishing to be bound by any particular theory, it is believed that adiponectin is a key effecter of hepatic steatosis and is secreted by adipose tissue. Expression of Ad36 E4orf1 protein alone, robustly increases adiponectin secretion by cells. This demonstrates that Ad36 lowers hepatic lipid accumulation via E4orf1 mediated upregulation of adiponectin. Also, Ad36 E4orf1 down regulates Glut2 abundance, and glucose release, which may contribute to lower lipid accumulation in the liver. Thus, it is believed that Ad36 protects from hepatic steatosis by direct effects on hepatocytes and via indirect effects through adiponectin, and that the E4orf1 protein is the mediator of these effects.

Therapeutic Methods

The invention provides therapeutic methods for treating or preventing NAFLD, reducing excessive fat from the liver, improving glycemic control and treating or preventing liver dysfunction.

In one aspect, the invention provides methods for the treatment and prophylaxis of symptoms of non-alcoholic fatty liver disease (NAFLD). A therapeutically effective amount of an Ad36 composition is administered to an individual (e.g., a mammal, such as a human or other primate) in need thereof to treat or prevent NAFLD.

In one aspect, the invention provides methods for the prevention of NASH. A therapeutically effective amount of an Ad36 composition is administered to an individual (e.g., a mammal, such as a human or other primate) in need thereof to prevent NASH by reducing hyperglycemia resulting from hepatic dysfunction In one aspect, the invention provides methods for reducing excessive fat from the liver of an individual (e.g., a mammal, such as a human or other primate). A therapeutically effective amount of an Ad36 composition is administered to an individual in need thereof to reduce excessive fat from the liver of the individual.

In one aspect, the invention provides methods for improving glycemic control in an individual (e.g., a mammal, such as a human or other primate). A therapeutically effective amount of an Ad36 composition is administered to an individual in need thereof to improve glycemic control in the individual.

In one aspect, the invention provides methods for treating or preventing liver dysfunction, characterized by fatty liver and/or insulin resistance. A therapeutically effective amount of an Ad36 composition is administered to an individual (e.g., a mammal, such as a human or other primate) in need thereof to treat or prevent liver dysfunction, characterized by fatty liver and/or insulin resistance.

In preferred embodiments of any of the methods described herein, the Ad36 composition that is administered is an isolated or recombinant Ad36 E4orf1 protein or functional variant thereof. In other embodiments of any of the methods described herein, the Ad36 composition that is administered is an isolated or recombinant nucleic acid that encodes Ad36 E4orf1 protein or functional variant thereof.

Ad36 Compositions

The Ad36 composition administered in accordance with the invention can have a variety of forms. Preferably, the composition comprises E4orf1 or a functional variant thereof. For example, the Ad36 composition can be the Ad36 virus or an attenuated variant, or an inactivated form of Ad36, such as a heat-killed or bleach-killed Ad36 or a replication deficient recombinant Ad36. The Ad36 composition can comprise an isolated or recombinant Ad36 protein, preferably the E4orf1 protein or a functional variant thereof. The Ad36 composition can comprise a nucleic acid encoding the E4orf1 protein or a functional variant thereof. The Ad36 composition can comprise an analog of E4orf1 protein, for example a chemical analog or structural analog.

Proteins and Peptides

The Ad36 composition can comprise an isolated or recombinant Ad36 protein, preferably the E4orf1 protein or a functional variant thereof.

Proteins or polypeptides referred to herein as "isolated" are proteins or polypeptides purified to a state beyond that in which they exist in infected mammalian cells. Ad36 proteins, including E4orf1 and functional variants thereof, can be produced using well-known methods, such as recombinant expression and purification, chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

As used herein "Ad36 E4orf1" refers to naturally occurring or endogenous E4orf1 proteins from Adenovirus 36, to proteins having an amino acid sequence which is the same as that of a naturally occurring or endogenous corresponding Ad36 E4orf1 (e.g., recombinant proteins), and to functional variants of each of the foregoing (e.g., functional fragments and/or mutants produced via mutagenesis and/or recombinant techniques). Accordingly, as defined herein, the term includes mature Ad36 E4orf1, glycosylated or unglycosylated Ad36 E4orf1 proteins, polymorphic or allelic variants, and other isoforms of Ad36 E4orf1 (e.g., produced by alternative splicing or other cellular processes), and functional fragments.

"Functional variants" of Ad36 E4orf1 include functional fragments, functional mutant proteins, and/or functional fusion proteins. Generally, fragments or portions of Ad36 E4orf1 encompassed by the present invention include those having a deletion (i.e. one or more deletions) of an amino acid (i.e., one or more amino acids) relative to the mature Ad36 E4orf1 (such as N-terminal, C-terminal or internal deletions). Fragments or portions in which only contiguous amino acids have been deleted or in which non-contiguous amino acids have been deleted relative to mature Ad36 E4orf1 are also envisioned. Generally, mutants or derivatives of Ad36 E4orf1, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of Ad36 E4orf1 differing by the addition, deletion and/or substitution of one or more contiguous or non-contiguous amino acid residues.

A "functional fragment or portion" of Ad36 E4orf1 refers to an isolated and/or recombinant protein or oligopeptide which has at least one property, activity and/or function characteristic of Ad36 E4orf1, such as attenuating hepatic steatosis, enhancing glucose disposal, and/or improving glycemic control.

Generally, the Ad36 E4orf1 or functional variant has an amino acid sequence which is at least about 85% similar, at least about 90% similar, at least about 95% similar, at least about 96% similar, at least about 97% similar, at least about 98% similar, or at least about 99% similar to SEQ ID NO:2 or SEQ ID NO:4 over the length of the variant.

In some embodiments, SEQ ID NO:1 or SEQ ID NO:3 are used to make purified protein of Ad-36 E4orf1, for example, using currently available recombinant protein production. Amino acid sequence identity can be determined using a suitable amino acid sequence alignment algorithm, such as CLUSTAL W, using the default parameters. (Thompson J. D. et al., Nucleic Acids Res. 22:4673-4680 (1994).)

Nucleic Acids and Vectors

The Ad36 composition can comprise an isolated or recombinant nucleic acid or vector encoding a protein of Ad36, preferably the E4orf1 protein or a functional variant thereof.

An isolated and/or recombinant (including, e.g., essentially pure) nucleic acids having sequences which encode an Ad36 E4orf1 protein or functional variant thereof can be administered to cause Ad36 E4orf1 production in situ. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Isolated and/or recombinant nucleic acids meeting these criteria comprise nucleic acids having sequences identical to sequences encoding naturally occurring Ad36 E4orf1 and portions thereof, or functional variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues. The sequence can be codon-optimized or codon de-optimized for expression in the individual.

In one aspect, the Ad36 E4orf1 or functional variant has a nucleic acid sequence which is at least about 85% similar, at least about 90% similar, at least about 95% similar, at least about 96% similar, at least about 97% similar, at least about 98% similar, or at least about 99% similar to SEQ ID NO:1 or SEQ ID NO:3 over the length of the variant. Nucleic acid sequence identity can be determined using a suitable nucleic acid sequence alignment algorithm, such as CLUSTAL W, using the default parameters. (Thompson J. D. et al., Nucleic Acids Res. 22:4673-4680 (1994).)

The nucleic acid can be in the form of DNA, RNA, and can be either single or double stranded. Generally, the nucleic acid is operably linked to expression control sequences such as an origin of replication, a promoter, and an enhancer (see, e.g., Queen, et al., Immunol. Rev. 89:49-68, 1986). A number of suitable vectors for expression of recombinant proteins in desired cells are well-known and conventional in the art Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell. If desired, the vector can include a detectable marker.

In certain embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are known.

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, 1988; Nicolas and Rubinstein, In: Vectors: A survey of molecular cloning vectors and their uses, Rodriguez and Denhardt, eds., Stoneham: Butterworth, pp. 494-513, 1988; Baichwal and Sugden, Baichwal, In: Gene Transfer. Kucherlapati R, ed., New. York, Plenum Press, pp. 117-148, 1986, 1986: Temin, In: Gene Transfer, Kucherlapati, R. ed. New York. Plenum Press, pp. 149-188, 1986). Preferred gene therapy vectors are generally viral vectors.

Administering Ad36 E4orf1

A variety of routes of administration are possible including, but not necessarily limited to parenteral (e.g., intravenous, intraarterial, intramuscular, subcutaneous injection), oral (e.g., dietary), topical, inhalation (e.g., intrabronchial, intranasal or oral inhalation, intranasal drops), or rectal.

The Adenovirus-36 E4orf1 protein can be administered by introducing into the mammal a nucleic acid sequence encoding the Adenovirus-36 E4orf1 protein, in a manner permitting expression of the Adenovirus-36 E4orf1 protein. In such method, the nucleic acid sequence can be introduced by a method selected from the group consisting of electroporation, DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, viral vectors, and naked DNA transfer.

Formulation of an Ad36 composition to be administered will vary according to the route of administration selected (e.g., solution, emulsion, capsule) and the individual to be treated. An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980). For inhalation, the compound is solubilized and loaded into a suitable dispenser for administration (e.g., an atomizer, nebulizer or pressurized aerosol dispenser), or formulated as a respirable dry powder.

The Ad36 composition can be administered in a single dose or multiple doses, A therapeutically effective amount is administered. A therapeutically effective amount is an amount sufficient to produce the intended effect under the conditions of administration. For example, an amount that is sufficient to increase fat oxidation, increase transport of fat out of the liver, to lower Glut2 abundance in the liver, to reduce G6 Pase in the liver, to enhance adiponectin, and/or Glut4, to improve glycemic control and/or to improve liver function can be administered. The appropriate dosage can be determined by a clinician of ordinary skill using methods known in the art, which take into consideration the individual's age, sensitivity to drugs, tolerance drugs, severity of disease and overall wellbeing, as well as other factors. Suitable dosages can be from about 0.1-about 10.0 mg/kg body weight per treatment.

Individuals who are administered Ad36 compositions can be screened through non-invasive testing, for example, using ultrasound, to determine whether the treatment was effective. In some aspects, the individual will be screened using ultrasound. In some aspects, the individual will undergo liver function testing to measure liver enzymes.

The entire teachings of all documents cited herein are hereby incorporated herein by reference.

Ad36 E4orf1 Sequences

```
Ad-36 E4 orf 1 DNA sequence
                                        (SEQ ID NO. 1)
ATGGCTGAATCTCTGTATGCTTTCATAGATAGCCCTGGAGG

GATCGCTCCCGTCCAGGAAGGGGCTAGCAATAGATATCTTCTTTTGCC

CCGAATCTTTCCACATTCCTCCGCATGGGTGATATTGCTTCACCTCAGA

GTGAGCGTGCTGGTTCCTACTGGATATCAGGGCAGATTTATGGCCTTGAA

TGACTACCATGCCAGGGGCATACTAACCCAGTCCGATGTGATATTTGCCG

GGAGAAGACATGATCTCTCTGTGCTGCTCTTTAACCACACGGACCGATTT

TTGTATGTCCGCGAGGGCCACCCAGTGGGAACCCTGCTGCTGGAGAGAGT

GATTTTTCCTTCAGTGAGAATAGCCACCCTGGTTTAG
```

```
Ad-36 E4 orf 1 Protein translation
                                        (SEQ ID NO. 2)
MAESLYAFIDSPGGIAPVQEGASNRYIFFCPESFHIPPHGV

ILLHLRVSVLVPTGYQGRFMALNDYHARGILTQSDVIFAGRRHDLS

VLLFNHTDRFLYVREGHPVGTLLLERVIFPSVRIATLV
```

```
Ad-36 E4 orf 1 ΔPDZ DNA sequence
                                        (SEQ ID NO. 3)
ATGGCTGAATCTCTGTATGCTTTCATAGATAGCCCTGGAGG

GATCGCTCCCGTCCAGGAAGGGGCTAGCAATAGATATCTTCTTTTGCC

CCGAATCTTTCCACATTCCTCCGCATGGGTGATATTGCTTCACCTCAGA

GTGAGCGTGCTGGTTCCTACTGGATATCAGGGCAGATTTATGGCCTTGAA

TGACTACCATGCCAGGGGCATACTAACCCAGTCCGATGTGATATTTGCCG

GGAGAAGACATGATCTCTCTGTGCTGCTCTTTAACCACACGGACCGATTT

TTGTATGTCCGCGAGGGCCACCCAGTGGGAACCCTGCTGCTGGAGAGAGT

GATTTTTCCTTCAGTGAGAATATAG
```

```
Ad-36 E4 orf 1 ΔPDZ protein translation
                                        (SEQ ID NO. 4)
MAESLYAFIDSPGGIAPVQEGASNRYIFFCPESFHIPPHGV

ILLHLRVSVLVPTGYQGRFMALNDYHARGILTQSDVIFAGRRHDLS

VLLFNHTDRFLYVREGHPVGTLLLERVIFPSVRI
```

EXEMPLIFICATION

The results of the studies disclosed herein revealed that there is a link between Ad36 infection in humans and lower hepatic lipid levels and better glycemic control, The results also demonstrate that the Ad36 E4orf1 protein is the mediator of the protective effect of the Ad36 virus and that the effect is likely mediated through altering the expression of several genes including adiponectin and Glut2 abundance. Thus, these studies disclosed herein show that Ad36, Ad36 E4orf1, and functional variants thereof can be used to treat or prevent NAFLD, reduce excessive fat from the liver of a mammal, improve glycemic control, and treat or prevent liver dysfunction.

Techniques and Assays:

Virus preparation. Ad-36 was obtained from American Type Culture collection (ATCC Cat# VR913) plaque purified and propagated in A549 cells (human lung cancer cell line) as described and used previously (45, 44). Ad-2 was also obtained from ATCC (Cat #VR846) and propagated in A549 cells. Viral titers were determined by plaque assay (45) and inoculations expressed as plaque forming units (PFU).

b. Biochemical Assays:

Glucose: 2 µL of serum from each mouse was measured in a 96-well plate format using Raichem glucose Oxidase method (R80038). Absorbance was read at 500 nm. Insulin: Ultra-sensitive mouse insulin ELISA kit (Crystal Chem, #90090) was used to determine insulin, Triglycerides were determined using Cardiochek Lipid panel test strips.

qRT-PCR: mRNA was extracted from adipose tissue of high-fat fed mice using the RNeasy Mini kit as per the manufacturer's instructions (Qiagen, #74101). Residual DNA was eliminated by using Amplification grade Deoxyribonuclease I (Invitrogen, #18068-015). One µg of total RNA was reverse transcribed to cDNA using Iscript™ cDNA synthesis kit (BioRad, #170-8890) as per the manufacturer's protocol. PCR core system II (Promega, # M7665) was used for the amplification of cDNA. Quantitative RT-PCR was performed to examine the relative expression levels of the genes TNFα (Tumor Necrosis factor alpha, Applied Biosystems, # Mm00443259_g1), Resistin (Applied Biosystems, # Mm00445641_m1), MCP-1 (macrophage chemoattractant protein; Applied Biosystems, # Mm00441243_g1) CD68 (Applied Biosystems, # Mm03047343_m1), TLR4 (Toll like receptor 4; Applied Biosystems, # Mm00445274_m1), MCSF (macrophage colony stimulating factor; Applied Biosystems # Mm00432688_m1), and IL6 (interleukin 6; Applied Biosystems, # Mm00446191_m1) as compared to GAPDH (glyceraldehydes 3 phosphate dehydrogenase; Applied Biosystems, # Mm99999915_g1). Means were compared by a T-test. Significance was set at p<0.05.

c. Confirmation of Infection:

Antibody Titer:

Presence of neutralizing antibodies in serum was determined by the 'constant virus-decreasing serum' method—a sensitive, specific and gold standard assay for determining neutralizing antibodies as described in detail (92). Briefly, heat inactivated test sera were serially diluted (two-fold) from 1:2 to 1:512 in 96-well plates. A total of 100 TCID-50 (Tissue culture infectivity dose 50) of the respective adenovirus work stock was added to each of the wells, followed by the addition of A549 cells after 1 h of incubation at 37° C. Each test serum was run in duplicate. Serum control (serum and cells, but no virus), cell control (cells alone, no virus, no serum), and virus control (cells and virus, no serum) were included with each assay. Plates were incubated at 37° C. for 13 days and the presence of CPE (cytopathic effect) was noted. Serum samples without CPE in dilutions of 1:8 or higher were considered positive for the presence of neutralizing antibodies to the respective virus and evidence of prior infection with that virus. Samples with titers lower than 1:8 were considered negative for the presence of viral antibodies. A virus backtitration was conducted with each assay as a quality check.

Screening for Viral DNA and RNA:

DNA isolation: DNA was isolated using a QIAMP DNA mini kit (#51306). Primers were designed to E4 gene of Ad36, Ad2 and also for mouse β-actin. DNA was amplified by PCR. The primer sequences were as follows:

```
Ad36 forward primer:
                                          (SEQ ID NO: 5)
5'-GGCATACTAACCCAGTCCGATG-3', Ad36 reverse primer:
                                          (SEQ ID NO: 6)
5'-TCACTCTCAGCAGCAGCAGG-3';

Ad2 forward primer:
                                          (SEQ ID NO: 7)
5'-CCTAGGCAGGAGGGTTTTTC-3', Ad2 reverse primer:
                                          (SEQ ID NO: 8)
5'-ATAGCCCGGGGGAATACATA-3'

Mouse β-actin forward primer:
                                          (SEQ ID NO: 9)
5'-GATCTTCATGGTGCTAGGAG-3', Mouse β-actin reverse primer:
                                          (SEQ ID NO: 10)
5'-ACGTTGACATCCGTAAAGAC-3'.
```

Negative PCR control: water. Positive PCR control: DNA from Ad36 or Ad2 infected A549 cells. DNA was denatured for 2 min at 95° C. and subjected to 35 cycles of PCR (94° C. for 1 min, 55° C. for 1 min, 72° C. for 2 min followed by incubation at 72° C. for 5 mins. RNA was extracted using the RNeasy Mini kit as per the manufacturer's instructions (Qiagen, #74101). Residual DNA was eliminated by using Amplification grade Deoxyribonuclease I (Invitrogen, #18068-015). One of total RNA was reverse transcribed to cDNA using Iscript™ cDNA synthesis kit (BioRad, #170-8890) as per the manufacturer's protocol. PCR core system II (Promega, # M7665) was used for the amplification of cDNA.

d. Glucose Tolerance Test:

Subsequent to a 16-h fast, conscious mice were injected with D-glucose (2.5 mg/g of body weight) intraperitoneally. Blood was collected from the tail vein prior to glucose injection (time 0) and at 10, 20, 30, 60, 120 and 150 min post-injection. Blood glucose was determined using a glucometer (Contour, Bayer).

e. Western Blot Analyses:

Immunoprecipitation: For immunoprecipitation of IR, IRS1 and IRS2, tissue samples were homogenized in a buffer containing 50 mM HEPES (pH 7.4). 2 mM sodium orthovanadate, 10 mM sodium fluoride, 2 mM EDTA, 1% NP-40, 0.25% sodium deoxycholate and protease inhibitors. Homogenates (250 μg) were then immunoprecipitated with 3 μg of primary antibody, Samples were subjected to SDS-PAGE using 4-20% gradient gel and transferred to PVDF membrane. The membranes were immunoblotted with anti-phospho antibodies. Antibodies for phoshphorylated-tyr-1322-IR-β (Millipore, #04-300) and total IR-β receptor (Millipore, #05-1104), total IRS1 (Santacruz, # Sc-559) and pIRS1-(tyr-989) (Santacruz, # Sc-17200), pIRS1-(ser307) (Cell signaling, #2381). IRS2 from (Milipore, #06-506) and p-IRS2 (tyr-612) from (Santacruz, # Sc-17195-R) were used.

Western Blot: Protein concentrations were quantitated by bicinchoninic acid assay and loaded to the 4-20% or polyacrylamide gel in equal amounts. Proteins were then transferred to a PVDF membrane. Membranes were blocked in PBS Tween-20 containing 3% BSA and incubated with polyclonal or monoclonal antibodies that recognize total AKT (Cell signaling, #4691), p-AKT(ser-473) (Cell signaling, #9271), Ras (Cell signaling, #3965), Glut1 (Abeam, #35826). Glut4 (Abeam, #14683), Glut2 (Santacruz, #9117), Glucose 6-Phosphatase (Santacruz, #7291), total AMPKα (Cell signaling, #2603), p-AMPKα(Thr-172) (Cell signaling, #2535) and leptin (Abeam, #2095) antibodies respectively. Followed by secondary antibody conjugated with horse reddish peroxidase, signals were detected by enhanced chemiluminiscence. The specific bands were quantitated with scanning densitometry using AlphaEaseFC analyzer software and equal loading was assessed by normalization to GAPDH (Ambion, #4300) abundance.

Analysis of different oligomeric forms of adiponectin: 30 μg of the protein isolated from adipose tissue was treated with 5Xnon-reducing buffer without DTT, β-mercaptoethanol and incubated for 1 h at room temperature. Samples were run on 4-20% Tris-Glycine SDS-PAGE gel and transferred to a PVDF membrane. Western blotting was performed using antiglobular domain antibody of adiponectin (Millipore, # MAB3608, Temmecula, Calif.).

f. Histochemistry:

Glycogen staining was performed on flash frozen liver samples of 3 mice each from Ad36. Ad2, and mock infected high fat fed mice, and one mock infected chow fed mouse as a control as reported (41). Tissue samples were embedded in OCT mounting medium and sliced at 8 um thickness. Glycogen was stained using periodic acid-schiff stain (PAS). Liver samples were fixed to enhance glycogen preservation and to help prevent streaming artifact in Carnoy's fixative (6 parts of ethanol, 3 parts of chloroform, and 1 part of glacial acetic acid) for 10 minutes at 4° C. Upon fixation, sections were washed in distilled water with several rinses and then incubated in 1% period acid solution for 5 minutes at room temperature. After washing with distilled water, Schiff's reagent was added and incubated for 11 minutes. All slides were rinsed in cold running tap water for 10 minutes. Slides were air dried and a cover slip was applied using permount. Glycogen staining gives a magenta color to the section with a darker stain indicating more glycogen.

Lipid leaves the sample during fixation, and thus white blank area on the slide indicates lipid droplets (96). Images were made with a Zeiss Axioskop 40 FL. Three specimens per sample and three images per specimen were analyzed using Image J for quantification of glycogen and lipid. Images were converted to 8 bit, and the threshold was determined where only glycogen specific staining was visible and the amount of glycogen was calculated as pixels2 at this threshold. This number was subtracted from the total area to obtain the area of blank space for quantification of lipid as reported (96).

Example 1

Ad36 and Humans

Serum samples from four cohorts were screened for Ad36 antibodies as an indicator of past infection. The cohorts were: A) HERITAGE Family Study (49) (n=671, White and Black men and women) B) PBRC (Pennington Biomedical Research Center) Study (206 White and Black men and women), C) MET Study (50, 51) (n=45 pre-pubertal White and Black boys and girls), D) VIVA LA FAMILIA study (52) (585 Hispanic boys and girls). The prevalence of Ad36 antibodies was 13%, 18%, 22% and 7% in the HERITAGE, PBRC, MET and Viva La Familia studies, respectively. Various measures of better glycemic control (including insulin sensitivity or disposition index) were significantly associated with Ad36 infection in these cohorts, independent of age, gender, race and adiposity (e.g. Tables 1 & 2 show the PBRC and MET cohorts). Importantly, the association of Ad36 with better glycemic control was remarkably consistent across these cohorts of diverse age groups and races of over 1,500 individuals. These data suggested that Ad36 infection may improve glycemic control in humans.

TABLE 1

PBRC study (n = 206; Black/White/Other 74/118/14) Mean (95% CI), adjusted for age, sex, race and body fat mass.

| N = 206 | Ad36−<br>N = 169 | Ad36+<br>N = 37 |
|---|---|---|
| Fasting glucose (mg/dL) | 96.9 (92.6, 101.3) | 92.3* (87.1, 97.6) |
| Fasting insulin (μU/ml) | 11.6 (9.6, 14.0) | 9.4* (7.1, 12.4) |
| HOMA IR | 2.7 (2.2, 3.3) | 2.1* (1.6, 2.8) |
| Liver density** (HU) | 10.7 (8.5, 13.4) | 13.0* (9.9, 17.2) |

*$p < 0.05$ or better.
**Normalized to spleen density.
Higher HU value equates to lower lipid content.

TABLE 2

MET Study, pre-pubertal boys and girls (n = 45; Black/White/Other; 10/32/3). Mean$^a$ (95% CI) adjusted for sex and body fat mass.

| N = 45 | Ad36−<br>N = 35 | Ad36+<br>N = 10 |
|---|---|---|
| Fasting glucose (mg/dL) | 74.5 (71.6-77.4) | 68.7* (62.9-74.6) |
| Fasting insulin (μU/ml) | 3.1 (2.4-4.1) | 1.8* (1.1-3.0) |
| HOMA IR | 0.51 (0.39-0.69) | 0.28* (0.16-0.48) |
| Intra-hepatic lipid (% water peak) | 0.005 (0.002-006) | 0.003* (0.004-0.008) |

$^a$Arithmetic mean for glucose; Geometric mean for insulin HOMA-IR and intra-hepatic lipid.

Example 2

Ad36 Improves Insulin Sensitivity in Chow-Fed Mice

Age, weight, and body fat matched female C57BL/6J mice were mock infected or infected with Ad36 or Ad2 and maintained on a standard chow diet. Four week old female C57B6/6J mice were purchased from The Jackson Laboratories (Bar Harbour, Me., USA). After 1 week of acclimatization, total body fat was determined by Bruker Minispec mq10 NMR (Nuclear Magnetic Resonance) analyzer. Mice were divided into three groups matched for body weight and body fat and inoculated intra-nasally, orally and intraperitoneally with 107 PFU of Ad36 (N=3) or Ad2 (a common human adenovirus used as a control; N=4) or mock infected with tissue culture media (n=6). The mice were on a 12 hour light-dark cycle at 25° C. and housed in micro-isolator cages under Biosafety level 2 containment in one room and offered ad libitum access to water and rodent chow (Purina LabDiet 5001).

The three groups of mice showed no difference in total body weight during a 12-week experiment.

Neutralizing antibodies to the adenoviruses, and/or PCR analyses for viral DNA and/or mRNA in various mouse tissues confirmed mock infection or infection by the expected virus (Table 3). Despite comparable fasting serum glucose and insulin levels between all three groups of mice at baseline prior to infection, these levels progressively decreased only in Ad36-infected mice over the course of the experiment (FIGS. 1A and B). Furthermore, at 12-weeks postinfection (pi), the masses of the retroperitoneal fat pad and liver of Ad36-infected mice were 2-fold higher ($p<0.03$) or 10% lower ($p<0.04$), respectively, than the mock infected mice (Table 4, FIG. 1). Thus, in standard chow-fed mice, Ad36 infection but not Ad2 infection improved systemic glycemic control by reducing fasting glucose and insulin levels.

TABLE 3

Percent of the mice showing viral antibodies, viral DNA & RNA.

| | Antibody | viral DNA/viral RNA | | |
|---|---|---|---|---|
| Group | Ad36/Ad2 | Liver | Adipose tissue | Lung | Kidney |

| Experiment 2: Chow-fed mice |
|---|
| Mock | 0/0 | | | 0/0 | |
| Ad36 | 100/100 | | | 100/100 | |
| Ad2 | 100/100 | | | 100/100 | |

| Experiment 3: Mice on high fat diet |
|---|
| Mock | 0/0 | 0/0 | 0/0 | 0/NA | 0/NA |
| Ad36 | 100/0 | 60/60 | 70/40 | 50/NA | 10/NA |
| Ad2 | 0/40 | 0/0 | 0/0 | 100/NA | 50/NA |

NA: Viral RNA not determined in these samples.

TABLE 4

Baseline and final characteristics of chow-fed mice. Mean ± SE.

|  | Mock | Ad36 | Ad2 | p |
|---|---|---|---|---|
| N | 6 | 3 | 4 | |
| Body weight (g)—week 0 | 16.3 ± 1.1 | 16.9 ± 0.21 | 16.2 ± 0.44 | NS |
| Body fat (g) week 0 | 2.1 ± 0.2 | 2.3 ± 0.2 | 2.0 ± 0.1 | |
| Body weight (g) week 12 | 22.3 ± 0.8 | 23.8 ± 1.7 | 22.5 ± 1.5 | NS |
| Retroperitoneal fat (g) week 12 | 0.18 ± 0.06 | 0.37 ± 0.15* | 0.25 ± 0.13 | *p < .05 vs Mock |
| Liver (g) | 1.00 ± 0.09 | 0.9 ± 0.1* | 0.99 ± 0.21 | *p < .05 vs Mock |

The body weights were measured once a week, and blood samples were obtained from the intra orbital retrobular sinus from anesthetized mice fasted for 4 hours. The mice were killed 12 weeks postinfection. Trunk blood was collected and serum was separated. Liver, retroperitoneal fat depots were carefully separated, weighed and flash frozen in liquid nitrogen and stored at −80° C. until use. Serum was used for determining glucose and insulin.

Differences in body weights, liver, fat pad weights, and glucose and insulin levels were analyzed by student's 't' test. Probability levels were set at p<0.05.

Example 3

Ad36 Improves Hyperglycemia in High-Fat Fed Mice

This experiment investigated whether Ad36 has similar effects in mice made diabetic with a high fat (HF, 60 kcal %) diet that causes diet-induced hyperglycemia.

Figure 2:
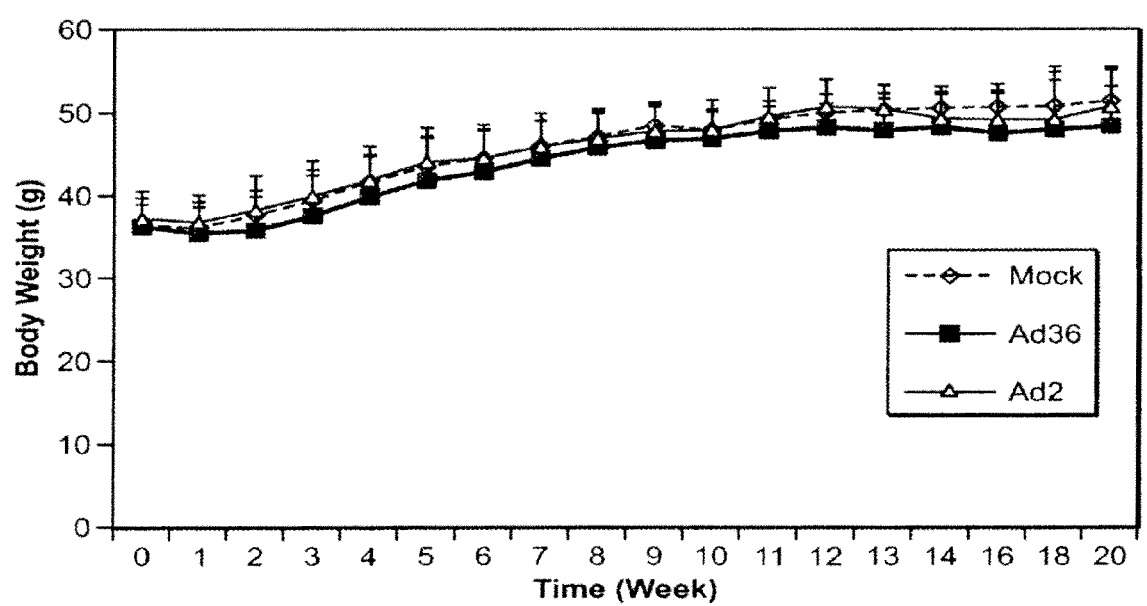
FIG. 2 is a graph showing body weight of high fat (HF)-fed mice.

Age, weight, and body fat matched male C57BL/6J mice (14 weeks old) fed a HF diet for the prior 8 weeks developed a diabetic state as evidenced by high fasting serum glucose levels (>200 mg/dL). At this point, mice were either mock infected or infected with Ad36, or Ad2. By 20 weeks pi, all three groups displayed similar cumulative food intake, as well as total body weight and fat pad masses (Table 5, FIG. 2). Fourteen week old male C57B6/6J mice were purchased from The Jackson Laboratory (Bar Harbour, Me., USA), who were fed a high fat (60% kcal) diet (Research Diets Inc. D12492i) starting at six weeks of age. Upon 1 week acclimatization, baseline body fat was determined by NMR and mice were divided in three groups (n=10 per group) matched for body fat and body weight. The groups were infected with Ad36 (0.6× 106 PFU), Ad2 (3×106 PFU) or mock infected intra-nasally, intra-peritoneally and orally, and continued on the high fat diet (60% kcal) for 20 more weeks. The mice were on a 12 hour light-dark cycle at 25° C. and housed singly in microisolator cages under Biosafety level 2 containment in one room. Food disappearance and body weights were measured once a week for 16 weeks, and blood samples were obtained from intra orbital retrobular sinus, in anesthesized mice. Fasting samples were collected after removing food for 4 hours. The mice were killed 20 weeks post-inoculation in free-fed state. Trunk blood was collected and serum was separated. Liver, epididymal, retroperitoneal fat depots were carefully separated, weighed and flash frozen in liquid nitrogen and stored at −80° C. until use.

Figure 3A:
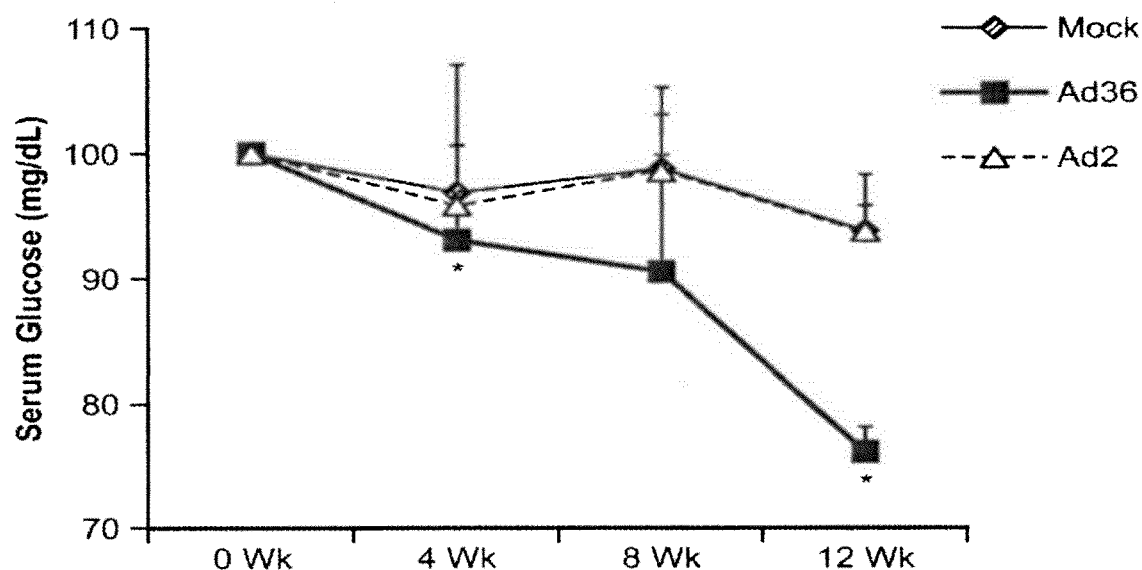
FIG. 3A is a graph showing the fasting serum glucose of chow-fed mice.
Figure 3B:
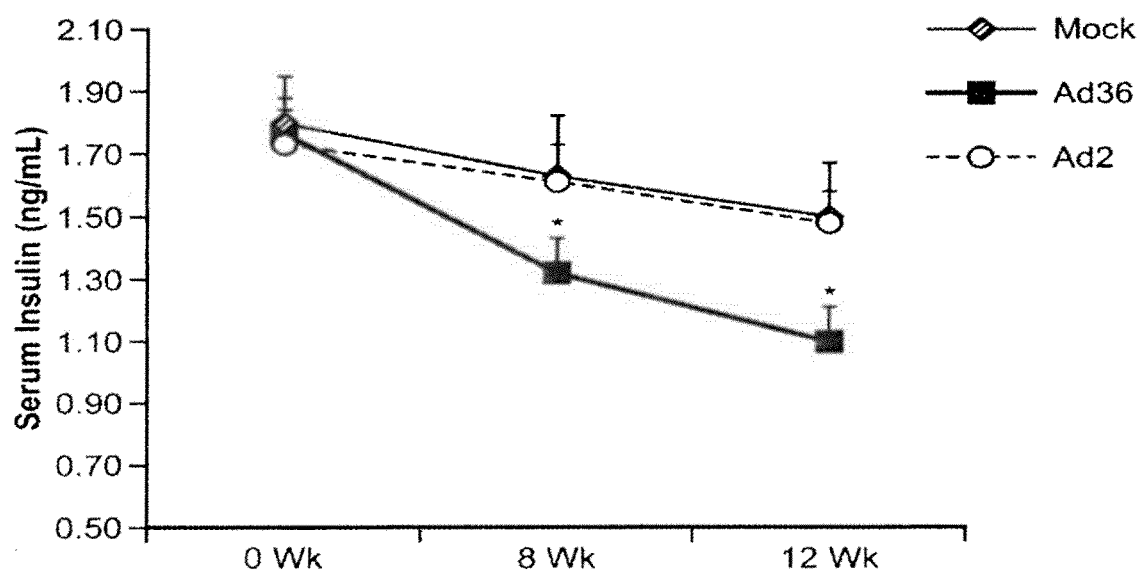
FIG. 3B is a graph showing the serum insulin of chow-fed mice.
Figure 3C:
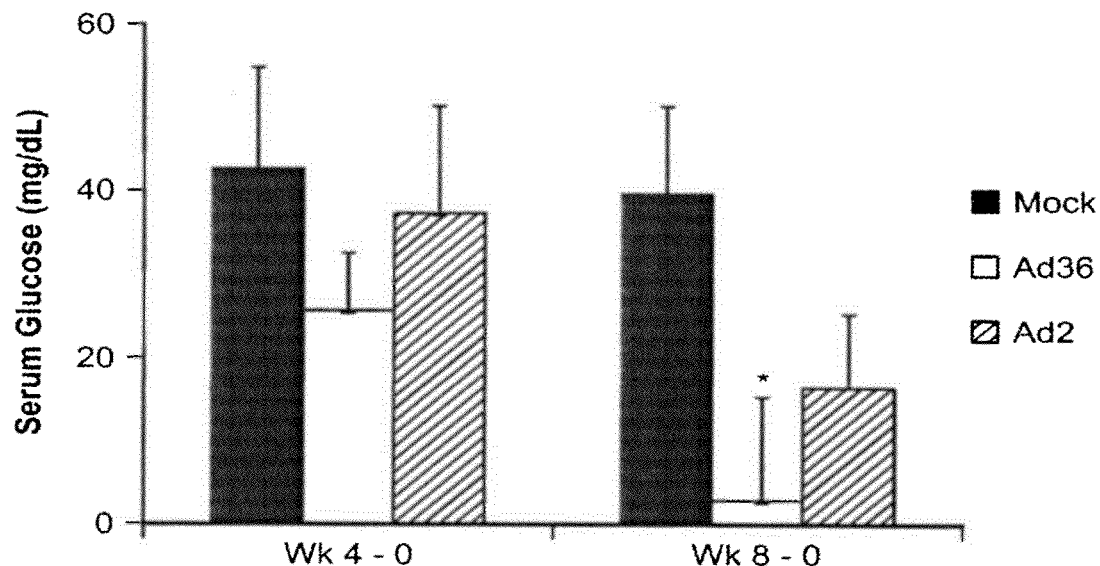
FIG. 3C is a graph showing the change in fasting serum glucose levels in HF-fed mice.
Figure 3D:
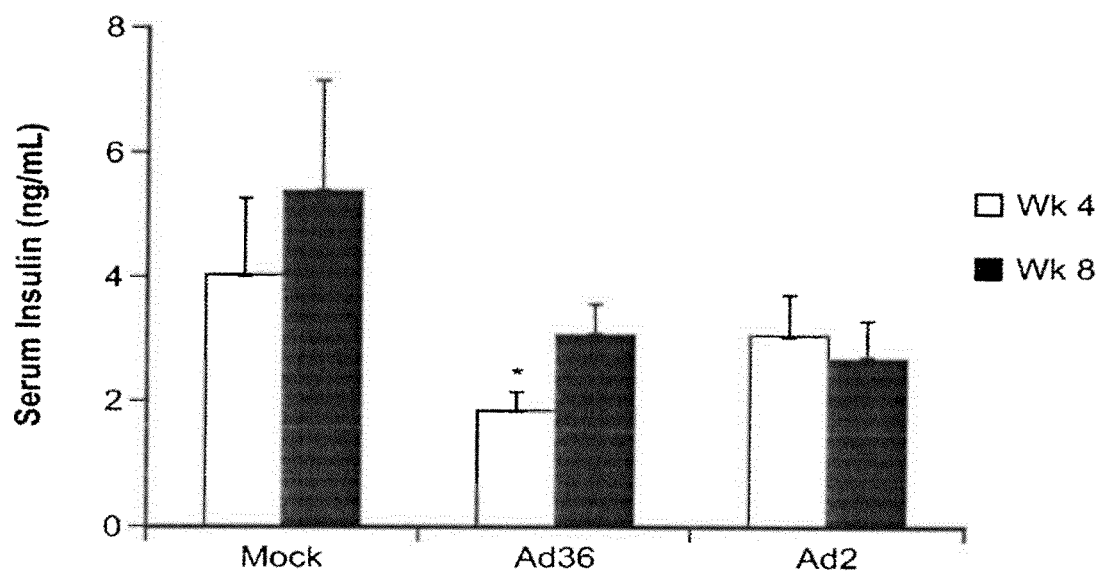
FIG. 3D is a graph showing the change in fasting serum insulin in HF-fed mice.
Figure 3E:
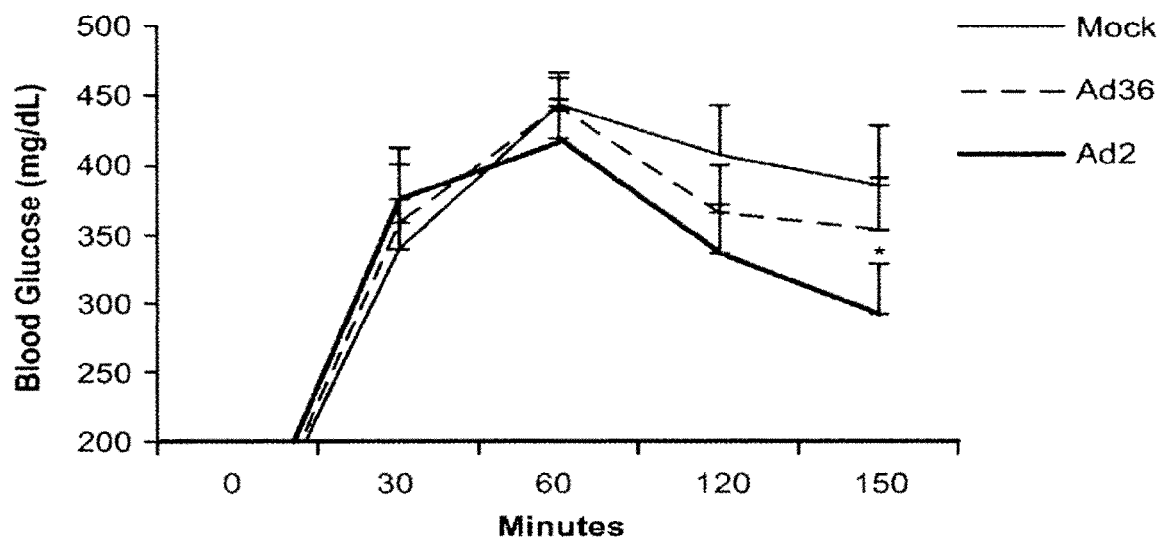
FIG. 3E is a graph showing the results of a glucose tolerance test 12 weeks post infection in HF-fed mice.
Figure 3F:
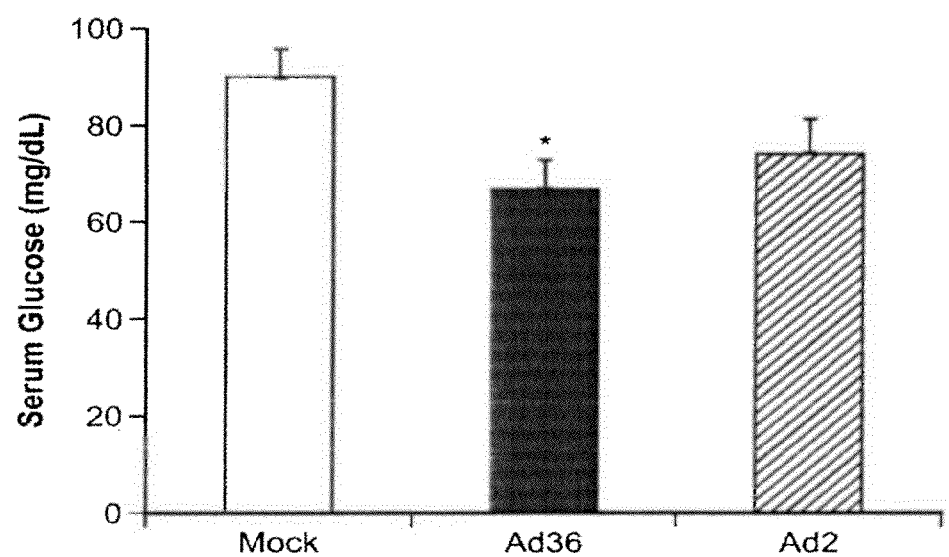
FIG. 3F is a graph showing free-fed serum glucose-20 weeks post infection in HF-fed mice.
Figure 4A:
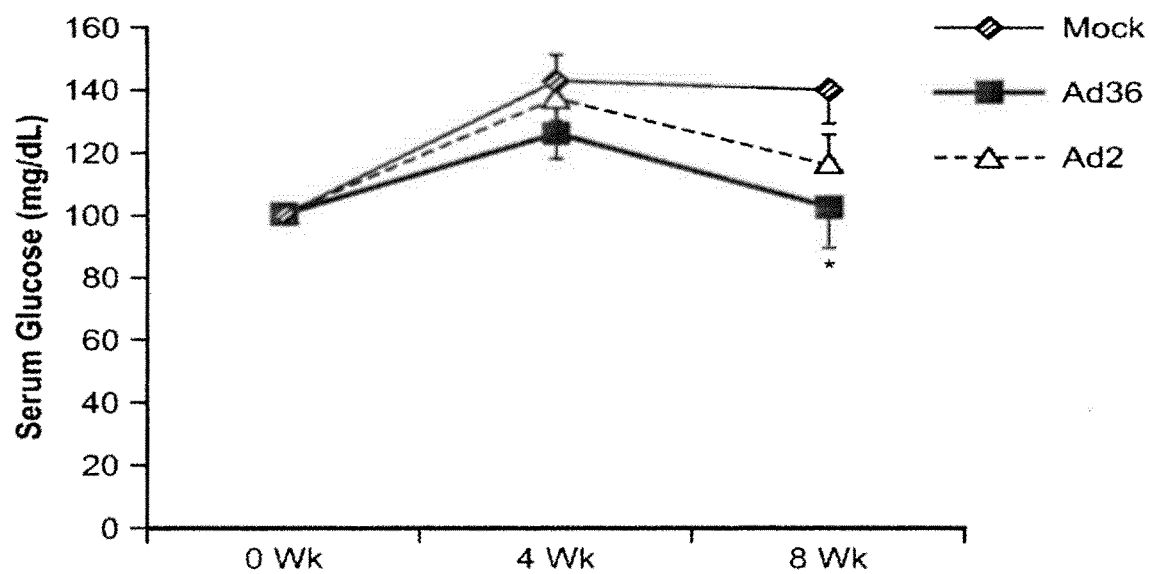
FIG. 4A is a graph showing the fasting serum glucose of HF-fed mice.
Figure 4B:
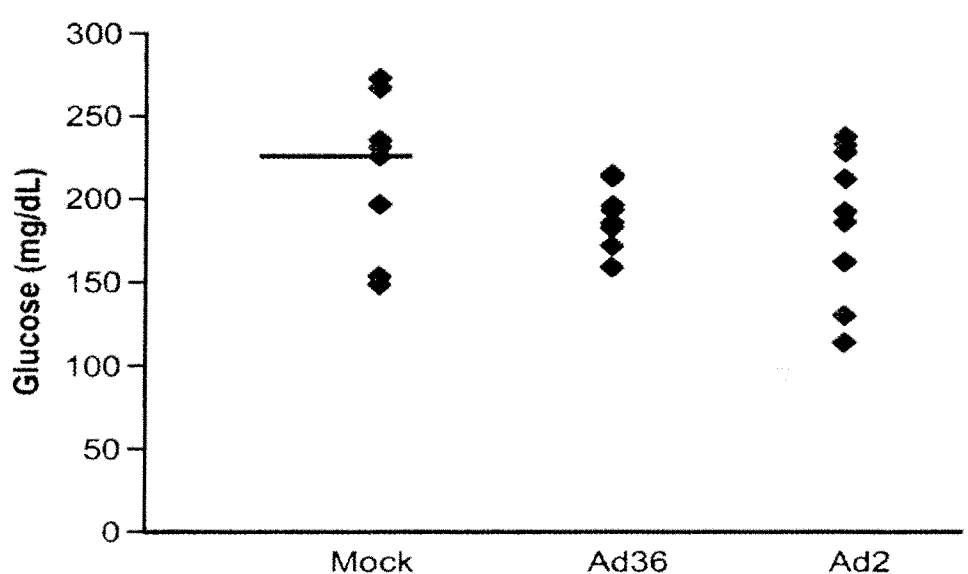
FIG. 4B is a graph showing free-fed serum glucose of HF-fed mice 20 weeks post infection.

Over the 20 week post-infection period, glycemic control was assessed in various ways, by determining fasting glucose and insulin, glucose tolerance test and also by determining glucose levels in free-fed state. As expected, due to HF diet-induced insulin resistance, mock-infected mice showed an increase in fasting serum glucose and insulin levels, however, these increases were significantly attenuated in Ad36-infected mice at 8 weeks pi or 4 weeks pi, respectively (FIGS. 3 C&D and 4A). Ad36-infected mice also showed significantly faster blood glucose clearance in response to an intraperitoneal glucose tolerance test (ipGTT) at 12 weeks pi (FIG. 3E) and lower free-fed serum glucose levels at 20 weeks pi (FIGS. 3F and 4B). In fact, at 20-weeks post-infection, free-fed serum glucose levels of all Ad36-infected mice were in the lower 50th percentile of those measured in mock-infected mice (FIG. 4B) (chi test p=0.01). Despite the 5-fold higher dose used for Ad2 versus Ad36 in this experiment, Ad2-infected mice still failed to show significantly improved dysglycemia compared to mocked-infected control mice. Therefore, Ad36 infection likewise specifically improves glycemic responses in diabetic mice under both fasted and fed conditions.

TABLE 5

Baseline and final characteristics of HF-fed mice. Mean ± SE.

|  | Mock | Ad36 | Ad2 | p |
|---|---|---|---|---|
| N | 10 | 10 | 10 | |
| Body weight (g) week 0 | 36.2 ± 0.9 | 36.1 ± 1.1 | 37.3 ± 1.0 | NS |
| Body weight (g) week 20 | 51.5 ± 0.8 | 48.3 ± 2.1 | 50.7 ± 1.2 | NS |
| Cumulative food Intake (g) (measured for 16 weeks post-infection) | 186 ± 9.2 | 186 ± 13.3 | 184 ± 13.7 | |
| Total body fat (g) week 0 Body fat (g) week 20 | 10.5 ± 0.8 | 10.7 ± 0.7 | 11.5 ± 1.0 | NS |
| Epididymal | 1.4 ± 0.05 | 1.4 ± 0.1 | 1.5 ± 0.2 | NS |
| Retroperitoneal | 0.5 ± 0.02 | 0.5 ± 0.05 | 0.5 ± 0.03 | NS |
| Liver (g) | 2.7 ± 0.1 | 2.3 ± 0.1* | 2.4 ± 0.2 | *p < .05 vs Mock |
| Serum triglycerides (mg/dL) | | | | |
| Week 0 | 71.6 ± 1.7 | 71.2 ± 0.9 | 71.5 ± 1.2 | *p < .05 vs week 0 of Ad36 |
| Week 8 | 70.4 ± 2.1 | 68.3 ± 1.2* | 69.3 ± 1.0 | |

Figure 5A:
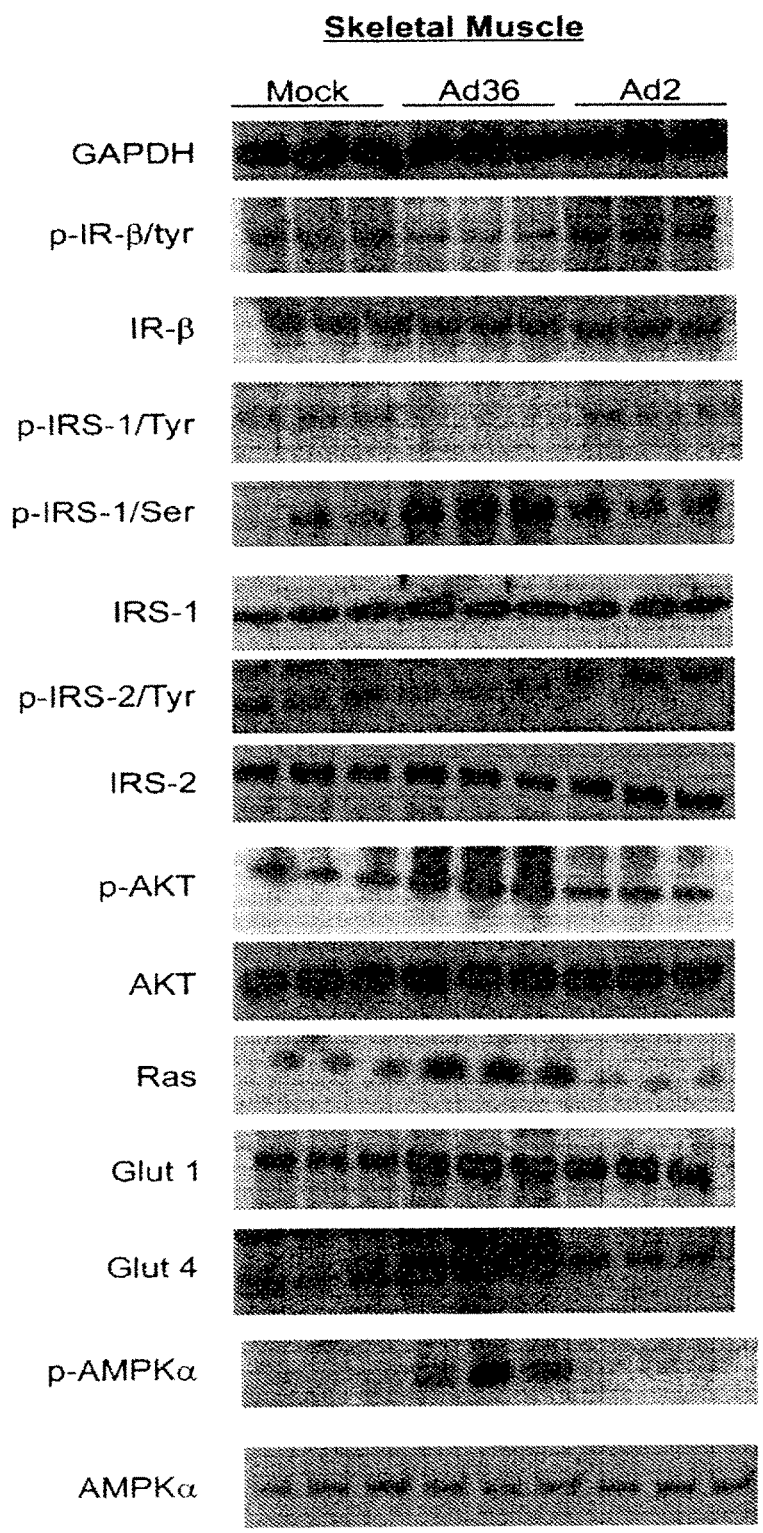
FIG. 5A is a Western blot showing protein abundance in skeletal muscle of HF-fed mice.
Figure 5B:
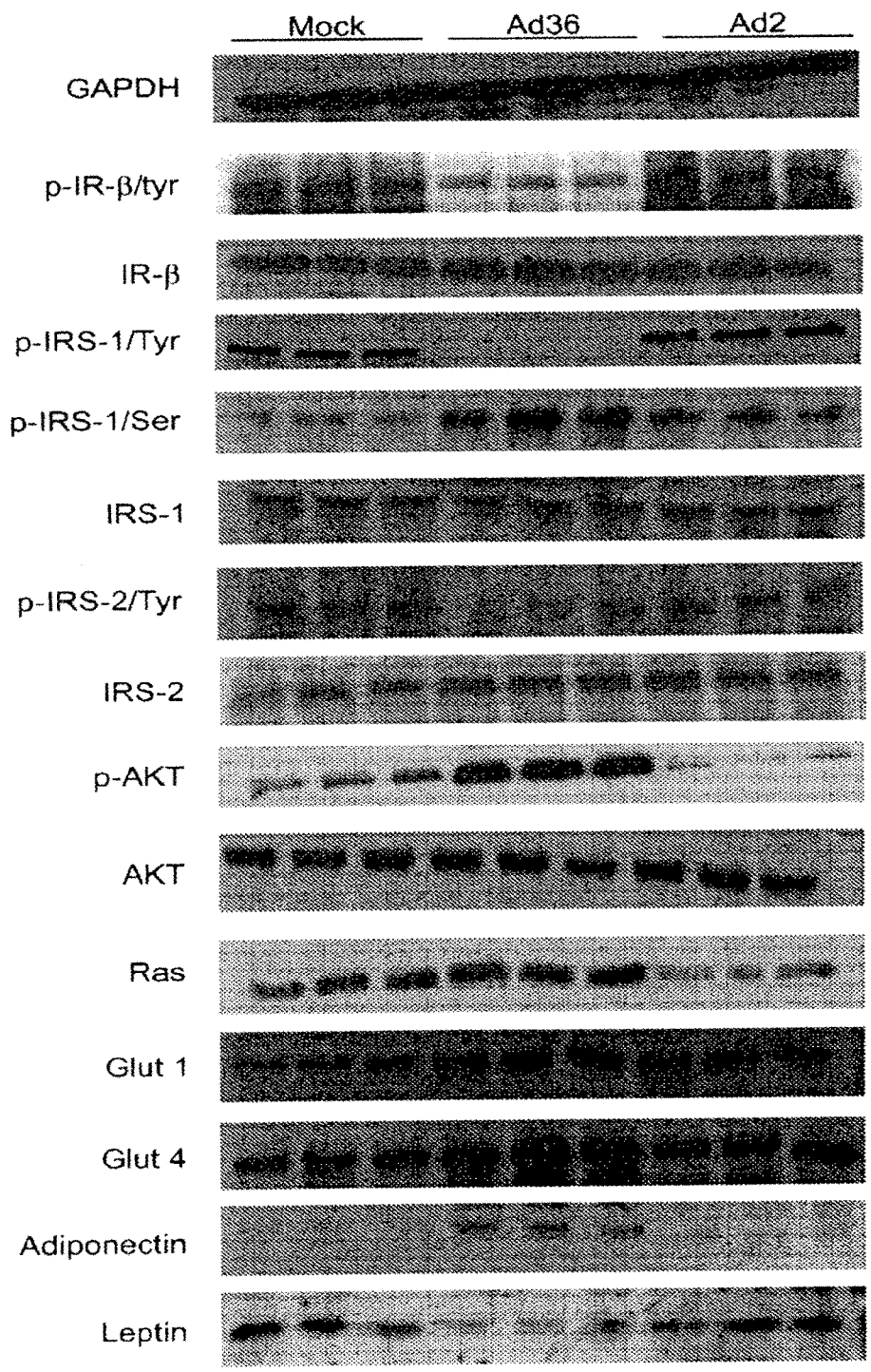
FIG. 5B is a Western blot showing protein abundance in adipose tissue of HF-fed mice.
Figure 5C:
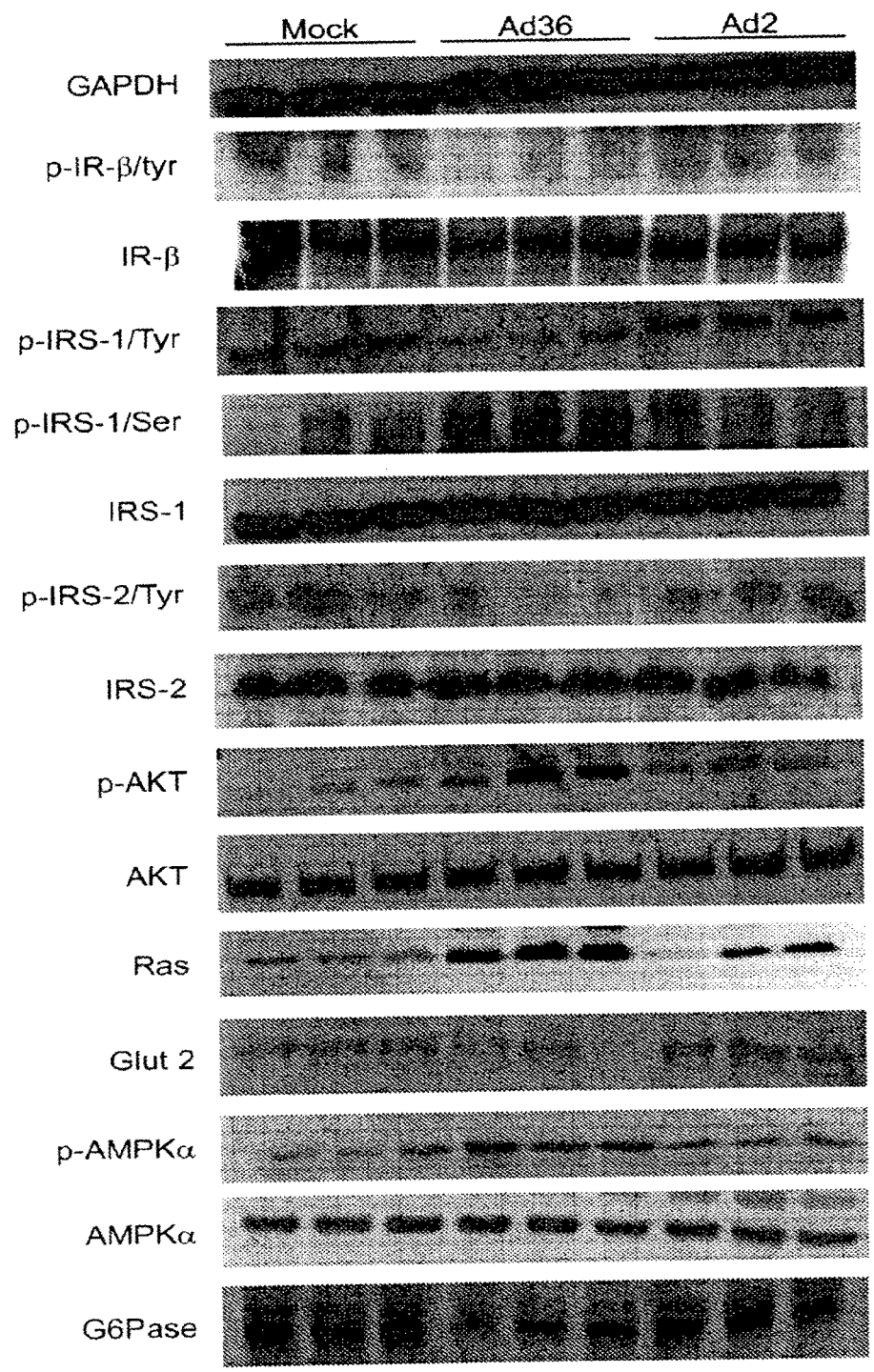
FIG. 5C is a Western blot showing protein abundance in livers of HF-fed mice.
Figure 6A:
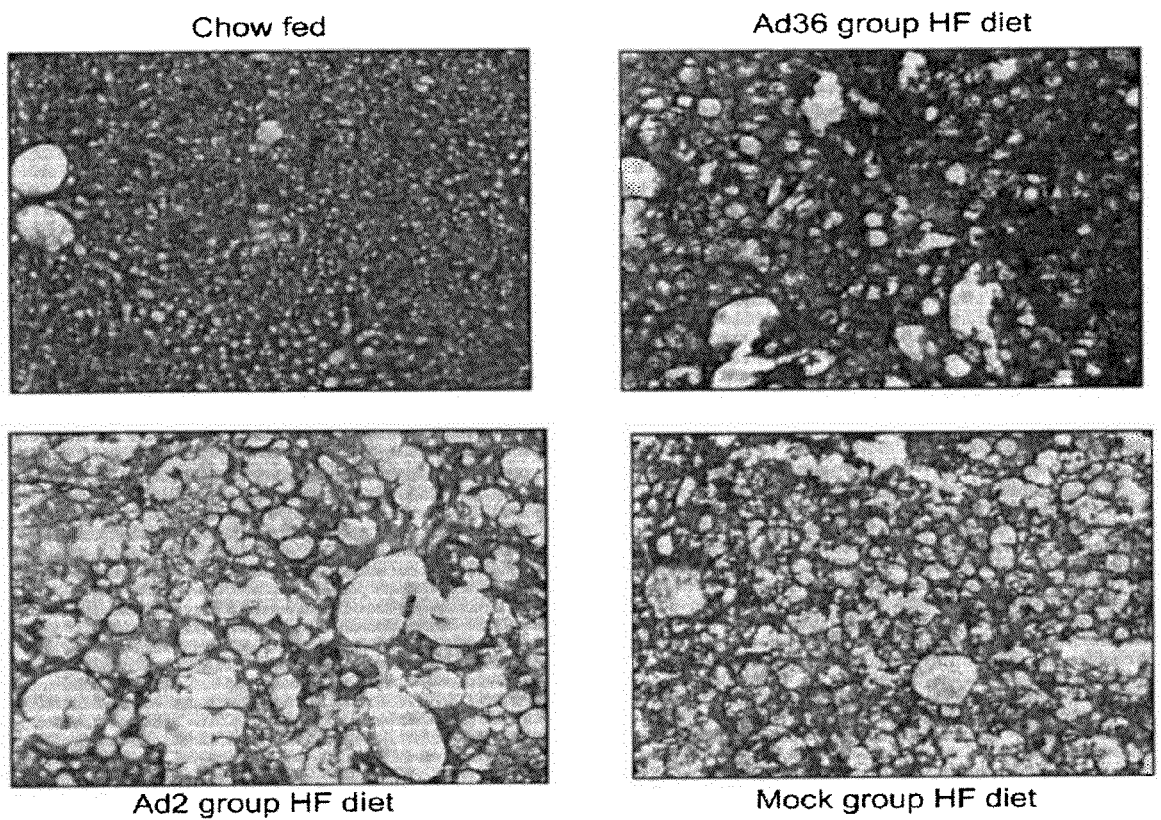
FIG. 6A is a panel of Periodic acid-Schiff stain of liver tissue of C57B1/6J mice. Dark stain shows glycogen and the white areas indicate lipid accumulation. Chow fed control mice show minimal lipid accumulation. The HF-fed groups showed greater lipid accumulation. However, Ad36, but not Ad2, significantly attenuated HF-diet induced steatosis, as indicated by lower lipid accumulation and greater glycogen (HF-fed Mock infected vs HF-fed Ad36 infected; $p<0.02$).
Figure 6B:
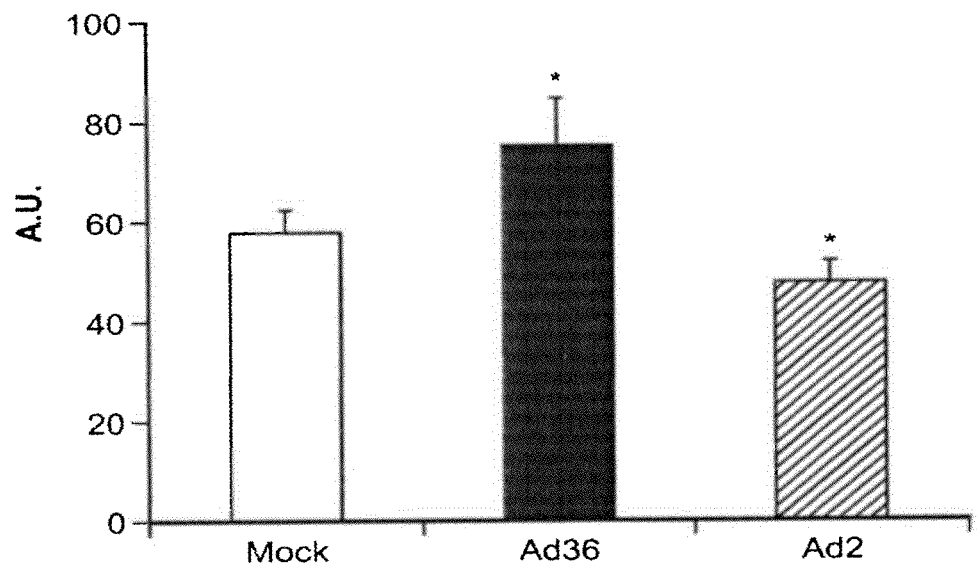
FIG. 6B is a graph showing the glycogen content of the liver sections of the HF-fed mice.
Figure 6C:
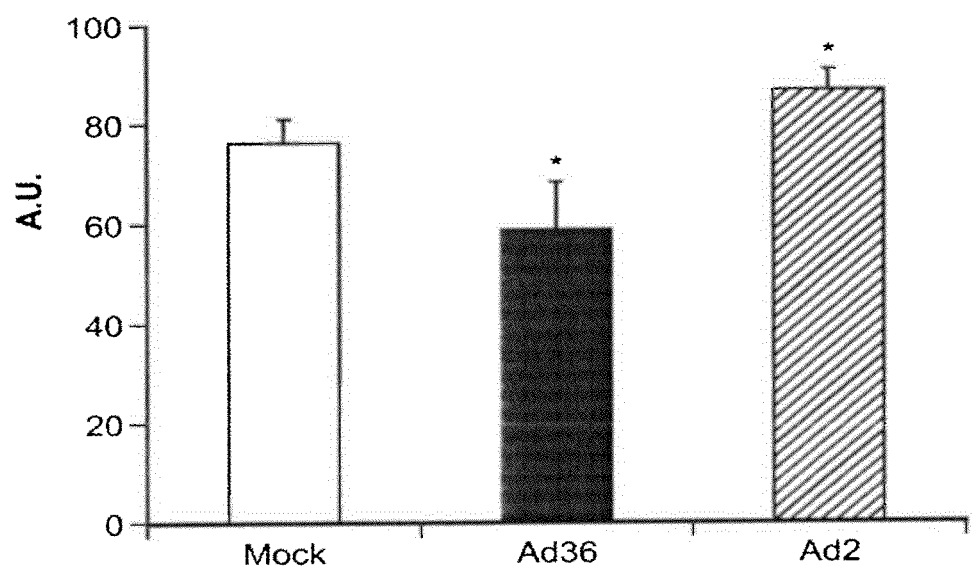
FIG. 6C is a graph showing the lipid content of the liver sections of HF-fed mice.

Western blot (WB) analyses conducted with mice from Example 2 revealed that in agreement with in vitro data (76, 12), Ad36 upregulated \Ras-PI3K pathway as indicated by greater abundance of Ras and phospho-Akt, in skeletal muscle, adipose tissue, and liver, compared to mock infected mice at 20 weeks pi (FIG. 5). For Ad36-infected mice, higher Glut4 and Glut1 protein abundance in skeletal muscle and adipose tissue suggested a mechanism by which Ad36 increases glucose uptake in these tissues, whereas lower Glut2 abundance and glucose-6-phosphatase (G6Pase) in the liver suggested that Ad36 decreases hepatic glucose release (FIG. 5C), which in turn may contribute to better glycemic control. As expected, liver sections of HF diet-fed mice displayed less glycogen and more lipid than did standard chow-fed mice (FIG. 6A). Among HF diet-fed mice, however, the livers of Ad36-infected mice showed higher protection from the pathological effects of the HF diet, as evidenced by increased glycogen and lower lipid content compared to mock-infected mice (FIGS. 6 A-C) (p<0.02). The protective effect mediated by Ad36 on HF diet-induced liver pathology is consistent with our human data, showing lower hepatic lipid accumulation in both, adults and pre-pubertal youth, infected with Ad36. Thus, findings presented here support a model whereby Ad36 increases glucose uptake by skeletal muscle and adipose tissue and reduces glucose release by the liver, thereby significantly improving systemic glycemic control in animals.

Differences in food intake, body weights, liver, fat pad weights, and glucose and insulin levels were analyzed by student's 't' test. Probability levels were set at p<0.05.

Example 4

Ad36 Improves Markers of the Metabolic Profile of Adipose Tissue

Figure 7A:
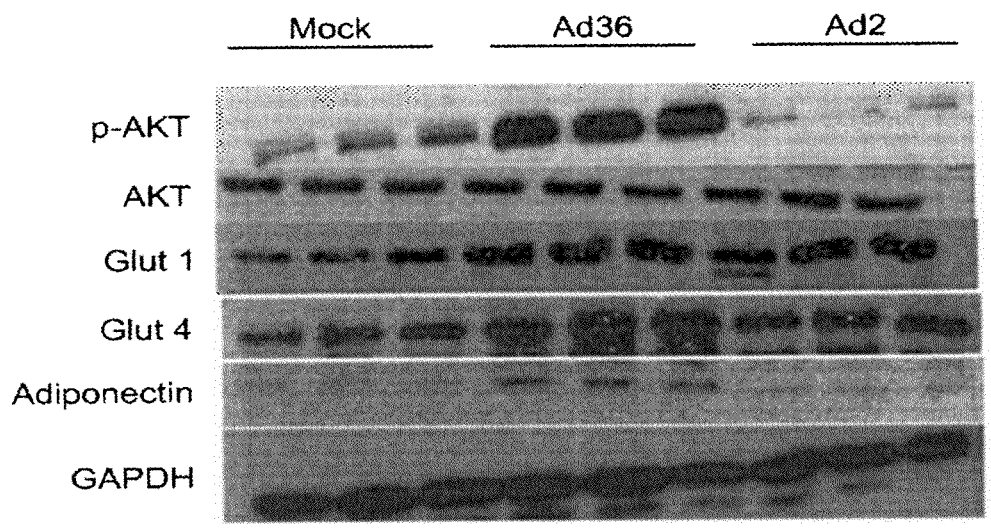
FIG. 7A: GAPDH was loading control. Compared to Mock, phospho-AKT. Glut1, Glut 4 & adiponectin were greater for Ad36 group ($p<0.05$), but not for Ad2.
Figure 7B:
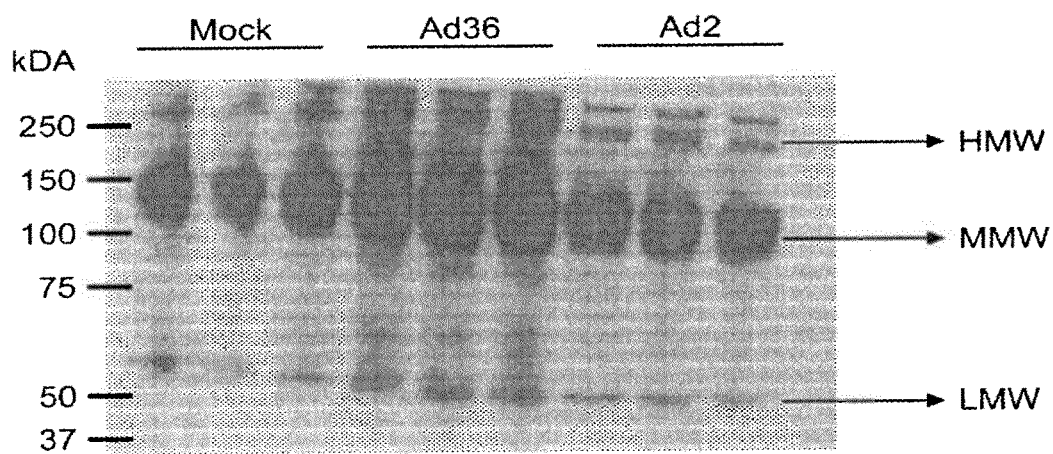
FIG. 7B: Compared to Mock, each of the adiponectin oligomers assayed under non-reducing, non-denaturing conditions were greater for Ad36, ($p<0.03$) but not for Ad2.

Western blots were run, as described above, using adipose tissue proteins from HF-fed mice killed in free fed state 20 weeks post-infection (3 mice/group). GAPDH was used as the loading control. Ad36 appears to up-regulate the PI3K pathway, and the downstream glucose uptake as indicated by greater AKT phosphorylation, and greater abundance of Glut4 and Glut 1. In response to infection, the adipose tissue in the Ad2, but not Ad36 group, had greater macrophage infiltration (p<0.05), compared to the Mock group. Importantly, the Ad36 group had a significantly greater abundance of adiponectin (FIG. 4A), a key insulin sensitizer and promoter of glucose uptake (53) and protector against hepatic steatosis (54) (55). Adiponectin exists in higher, medium, and lower molecular weight (MW) forms, though the higher MW form is most strongly linked to insulin sensitivity (56, 57). Ad36 significantly increased levels of all forms of adiponectin in the adipose tissue of HF diet-fed mice (FIG. 7B). The up-regulation of adiponectin by Ad36 was consistently observed, including its significantly greater mRNA and protein abundance in human adipose tissue explants infected with Ad36 (12). These changes collectively indicate that Ad36 improves the metabolic quality of the adipose tissue. Considering the strong hepatic effects of adiponectin (54, 55), it is believed that the adiponectin is a key mediator of anti-steatosis effect of Ad36.

Example 5

Ad36 Attenuates Steatosis and Improves Metabolic Profile in the Liver

Figure 8:
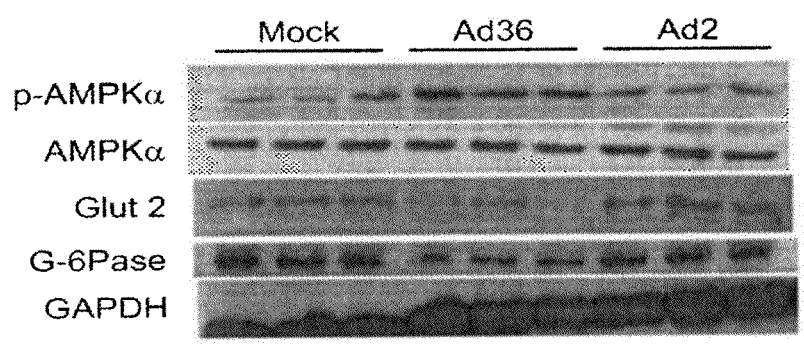
FIG. 8 shows Western blots using liver proteins of HF-fed mice. Compared to Mock, p-AMPK was greater and Glut2 and G6pase were lower for Ad36 ($p<0.05$), but not Ad2.

Liver sections of HF diet-fed mice displayed less glycogen and more lipid than did standard chow-fed mice (FIG. 6A). Among HF diet-fed mice, however, the livers of Ad36-infected mice showed higher protection from the adverse effects of HF diet, as evidenced by increased glycogen and lower lipid content compared to the Mock group (FIG. 6A) (p<0.02). Lower Glut2 abundance and glucose-6-phosphatase (G6Pase) in the livers of the Ad36 group (FIG. 8) suggested reduced hepatic glucose release, which in turn may contribute to better glycemic control. Livers of Ad36, but not Ad2 group, showed greater AMPK-phosphorylation, a known target of adiponectin to protect liver against steatosis (54).

Figure 9A:
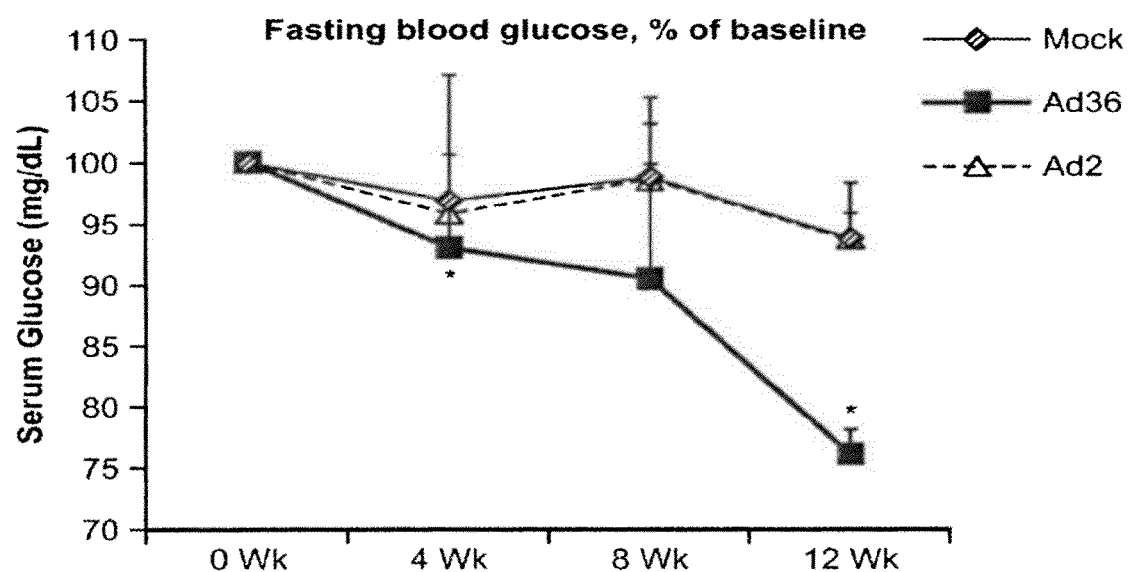
FIGS. 9A and 9B are graphs showing fasting blood glucose (A) and fasting serum insulin (B) at baseline (week 0) and up to 12 weeks post infection in chow-fed mice. *$p<0.05$ vs to Mock.
Figure 9B:
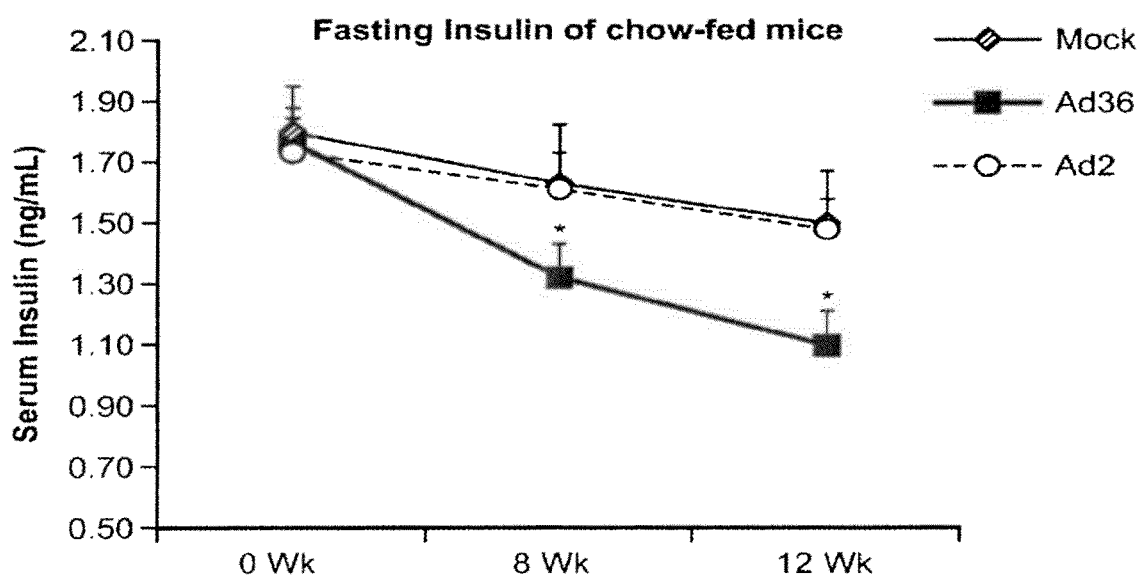
Figure 10A:
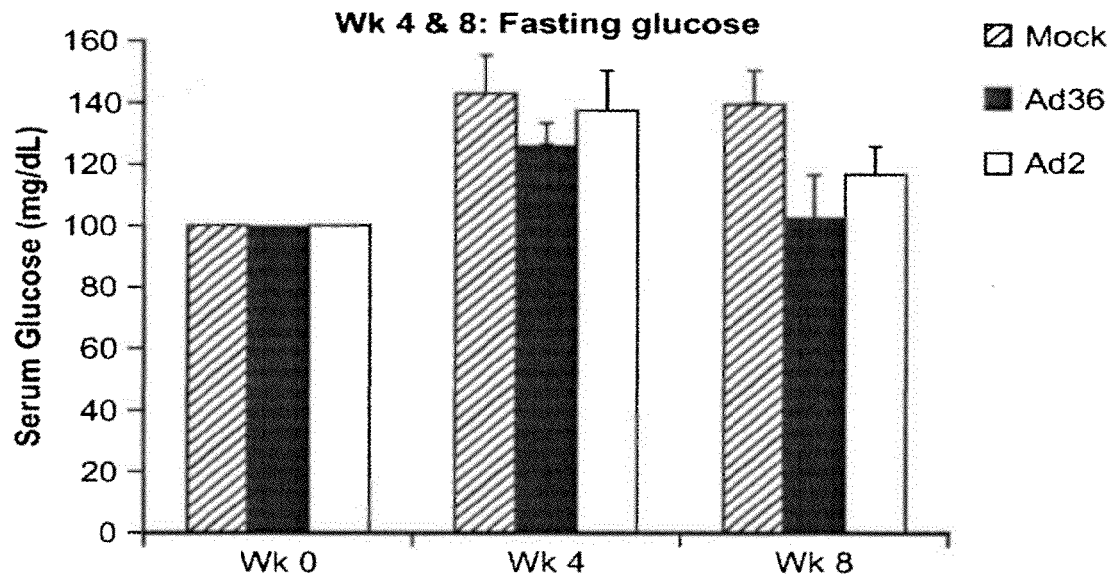
FIGS. 10A-D are graphs showing serum glucose and insulin time course in Ad36, Ad2 or mock groups post infection in mice on HF diet. (A) Weeks 4 and 8: fasting serum glucose adjusted to baseline (week 0). (B): Week 12: i.p. glucose tolerance test after 2.5 mg/g body weight. (C): Week 20: free-fed glucose. (D): change in fasting insulin from week 0. *$p<0.05$ or less, compared to Mock of respective studies.
Figure 10B:
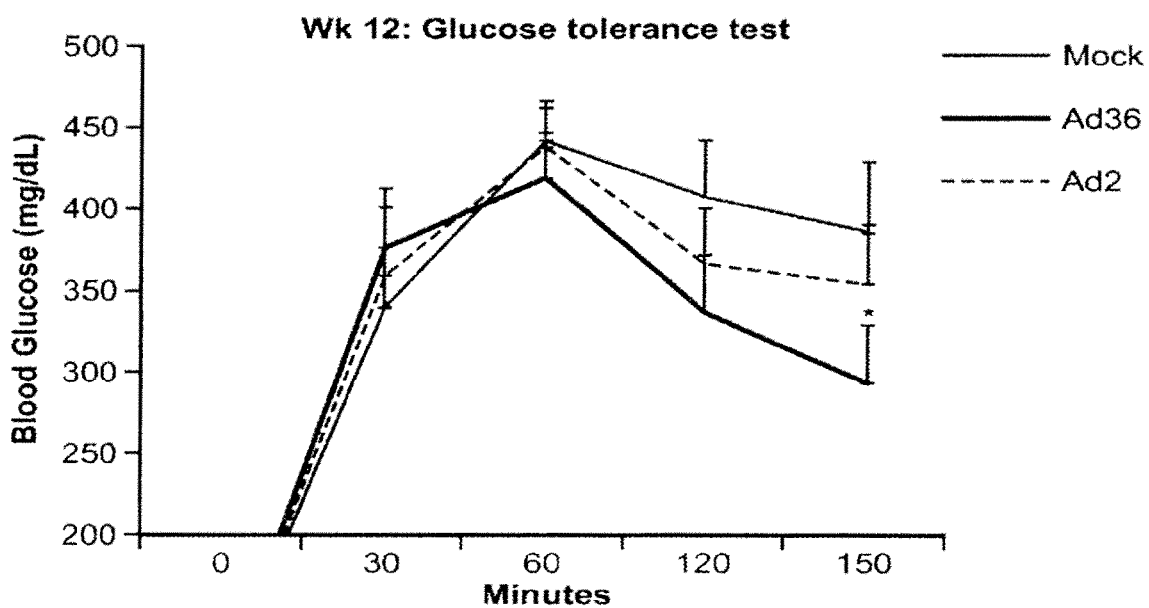
Figure 10C:
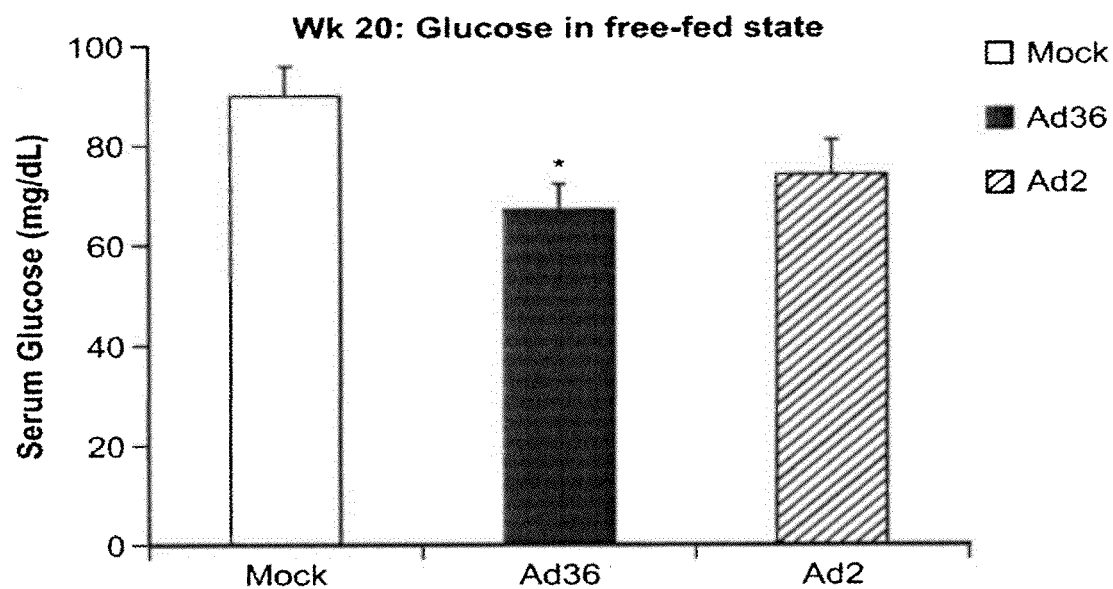
Figure 10D:
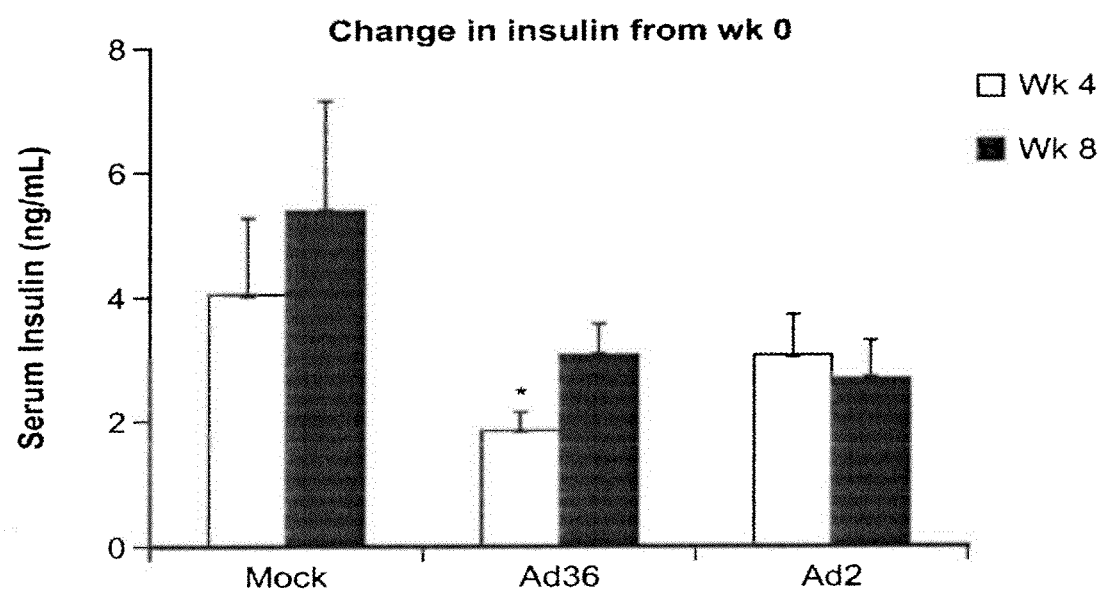

Liver mRNA: Expressions of selected genes from the livers of chow fed (FIG. 9) or HF-fed mice (FIG. 10) were tested. Although these molecules also perform overlapping roles in multiple pathways, we considered FAS (fatty acid synthase), SREBP1c (sterol response element binding protein 1c) and FOXO1 (Forkhead Box O1) as modulators of lipogenesis (58), CPT1 (carnitine palmityl acyl transferase), LXR (liver X receptor) and PPARα to indicate lipid oxidation (59-61) and MTP (microsomal triglyceride transfer protein) and ApoB (apolipoprotein B) as indicative of lipid export (62-66). Since hepatic steatosis coupled with inflammation may signal progression to NASH, markers of inflammation were determined. The hepatic gene expressions were determined 12-20 wk post inoculation (Table 3). While such a long period and a HF diet may mask some changes, the gene expressions from the chow fed and HF-fed mice collectively suggest that Ad36 reduces lipogenesis, up-regulates lipid oxidation and export and reduces inflammation in the liver (Table 6).

TABLE 6 qRT-PCR data of expression of genes in livers of mice fed chow or HF diets. Arrows indicate the direction of changes induced by Ad36 compared to the mock infected group.

| | Lipogenesis | | | Lipid oxidation | | | | | Lipid export | | Inflammation | | | |
|---|---|---|---|---|---|---|---|---|---|---|---|---|---|---|
| Diet | FAS | SREBPIC | FOXO1 | AdipoR1 | AdipoR2 | CPT1 | LXR | PPARα | ApoB | MTP | IL6 | IL10 | INFγ | TNFα |
| Chow | NS | NS | ↑* | ↑* | ↑* | ↑* | NS | ↑* | ↑* | ↑* | ↓ (.06) | NS | NS | NS |
| HF | NS | ↑ (.08) | ↑ (.07) | NS | NS | NS | NS | NS | ↑* | NS | ↓* | NS | ↓* | ↓* |

*p < .05 or better. To indicate trend, p value is also denoted, if between .05 and 0.1.
NS: no significant difference.

Example 6

Ad36 E4orf1 to Attenuate Hepatic Steatosis Without Weight Loss

In separate experiments, HepG2 cells, or mouse primary hepatocytes were transfected with E4orf1 or the empty pcDNA vector. Palmitate oxidation and apoB secretion by HepG2 cells and basal and glucagon stimulated glucose output by primary hepatocytes were determined 48 hours post transfection.

Compared to null vector transfected cells, E4orf1 increased fat oxidation 2-fold (p<0.0001), and apoB secretion 1.5 fold (p<0.003) and reduced basal and glucagon stimulated glucose output by 45% (p=0.0008) and 22% (p<0.02), respectively.

This in vitro transfection of hepatocytes shows that E4orf1 mediates the effects of Ad36 on hepatic metabolism. The data show that in hepatocytes, Ad36 E4orf1 increases fat oxidation and transport of fat outside the liver, and reduces glucose release.

Example 7

E4orf1 Induces PPARγ

PPARγ is the master regulator of adipogenesis, the process by which the body makes fat cells. Ad36 up-regulates PPARγ, induces adipogenesis, increases adiponectin and improves glycemic control. This study investigated whether adiponectin expression could be uncoupled from PPARγ induction or adipogenesis.

The following cell types were infected with human adenoviruses Ad36, or Ad2, or mock infected: a) 3T3-L1 mouse embryonic fibroblasts (MEF) with intact PPARγ; b) NIH/3T3 MEF which have impaired PPARγ expression; and c) MEF from PPARγ knockout mice (MEF−/−). Despite the down-regulation or the absence of PPARγ, Ad36 enhanced cellular glucose uptake, adiponectin, Glut4 and Glut1 protein abundance, versus mock or Ad2 infected cells. As expected, adipogenic induction increased lipid in 3T3-L1 but not NIH/3T3 or MEF−/−. This indicated that Ad36 up-regulates glucose uptake and adiponectin secretion without recruiting PPARγ or enhancing adipogenesis. In humans, natural Ad36 infection as determined by the presence of Ad36 antibodies, predicted higher adiponectin levels, suggesting therapeutic relevance of these effects. This further strengthens our proposition that it is possible to improve glucose uptake by E4orf1, without increasing body fat, unlike the action of TZDs.

Example 8

E4orf1 Protein Enhances Glucose Disposal

A stable 3T3-L1 cell line that inducibly expresses E4orf1 in response to doxycyclin (3T3-E4) was developed to study cell signaling and to test whether Ad36 requires its E4orf1 protein for up-regulating glucose uptake in 3T3-L preadipocytes. Compared to mock infected cells, Ad36 increased basal glucose uptake by 3-fold, which was abolished when E4orf1 was knocked down with siRNA. This showed that Ad36 enhances cellular glucose uptake via E4orf1. Compared to cells with null vector, 3T3-E4 cells increased glucose uptake in an induction dependent manner. E4orf1 increased the abundance and activation of Ras—the obligatory molecule in Ad36 induced glucose uptake. In particular, E4orf1 activates the H-Ras isoform. Thus, E4orf1 narrows down the antihyperglycemic effects of Ad36 to a single protein.

Example 9

E4orf1 Modulates Glucose Disposal in Adipocytes and Hepatocytes

In separate experiments, 3T3-L1 preadipocytes or adipocytes, C2C12 myoblasts or HepG2 hepatocytes were transfected with V-5 tagged plasmids expressing E4orf1 (pcDNA-V5-AD36-E4orf1) or a null vector (pcDNA-V5-DEST).

Considering that the glucose uptake by adipose tissue and skeletal muscle and glucose output by the liver contribute to systemic glycemic control, the effect of Ad36 E4orf1 on basal and insulin stimulated glucose disposal by cell lines representing these tissues was determined. Glucose disposal in 3T3-L1 preadipocytes or adipocytes, C2C12 myoblasts or HepG2 hepatocytes transfected with E4orf1 expressing plasmid was compared with cells transfected with a null vector.

Figure 11A:
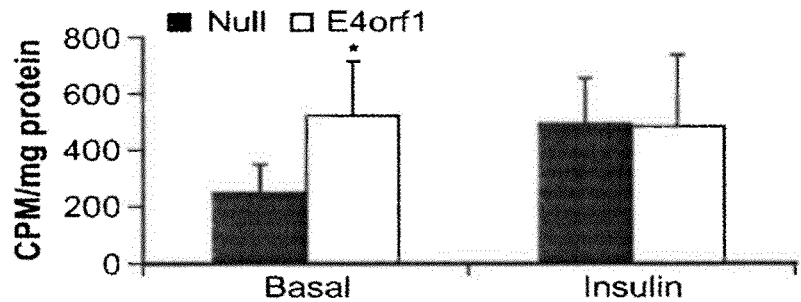
FIGS. 11A-C are graphs showing E4orf1 expression significantly increased basal 2DG glucose uptake in 3T3-L1 (A) preadipocytes, (B) adipocytes and (C) C2C12 myoblasts.
Figure 11B:
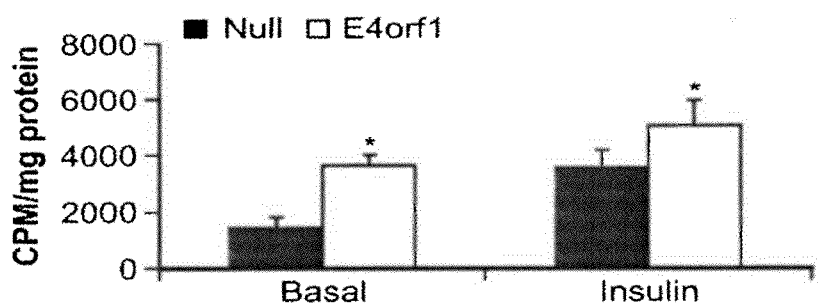
Figure 11C:
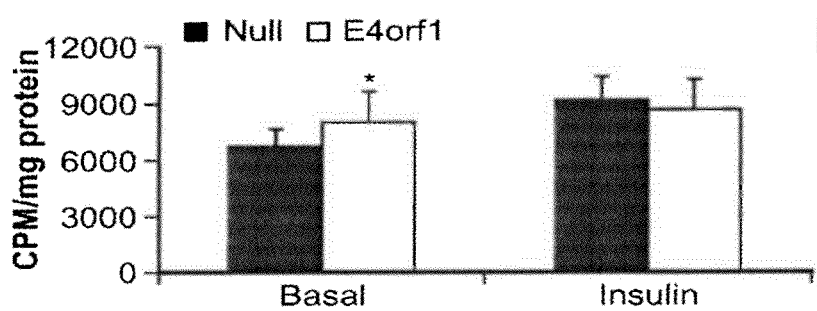
Figure 11D:
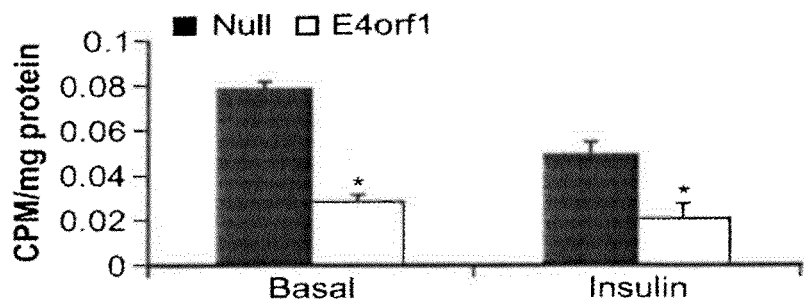
FIG. 11D is a graph showing E4orf1 expression significantly reduced glucose output by HepG2 cells under basal as well as insulin stimulated conditions.

E4orf1 expression increased basal 2DG uptake in 3T3-L1 preadipocytes, adipocytes and C2C12 myoblasts (FIGS. 11A-C). In adipocytes, E4orf1 further increased insulin stimulated 2DG uptake (p=0.003). In preadipocytes and myoblasts, which are not fully insulin responsive, E4orf1 did not enhance insulin stimulated 2DG uptake.

Although multiple metabolic functions of the liver such as glucose uptake, glycogen synthesis, glycogenolysis, contribute to systemic glycemic control, hepatic glucose output is often uncontrolled due to insulin resistance, and can be a key contributor of high blood glucose in type 2 diabetes, Therefore, the focus was on determining the effect of E4orf1 on glucose release by hepatocytes. E4orf1 transfection significantly reduced glucose output by HepG2 cells under basal as well as insulin stimulation conditions (p<0.000001 and <0.001, respectively; FIG. 5D).

This experiment shows that Ad36 E4orf1 influences glucose disposal by adipose tissue, skeletal muscle and liver.

REFERENCES

1. Fabbrini E, Magkos F, Mohammed B S et al. Intrahepatic fat, not visceral fat, is linked with metabolic complications of obesity. Proc Natl Acad Sci USA 2009; 106:15430-15435.
2. Deivanayagam S, Mohammed B S, Vitola B E et al. Nonalcoholic fatty liver disease is associated with hepatic and skeletal muscle insulin resistance in overweight adolescents. Am J Clin Nutr 2008; 88:257-262.
3. Targher G, Bertolini L, Padovani R et al. Prevalence of nonalcoholic fatty liver disease and its association with cardiovascular disease among type 2 diabetic patients. Diabetes Care 2007; 30:1212-1218.
4. Bellentani S, Scaglioni F, Marino M, Bedogni G. Epidemiology of non-alcoholic fatty liver disease. Dig Dis 2010; 28:155-161.
5. Parekh S, Anania F A. Abnormal lipid and glucose metabolism in obesity: implications for nonalcoholic fatty liver disease. Gastroenterology 2007; 132:2191-2207.
6 Adams L A, Lymp J F, St Sauver J et al. The natural history of nonalcoholic fatty liver disease: a population-based cohort study. Gastroenterology 2005; 129:113-121.
7. Ekstedt M, Franzen L E, Mathiesen U L et al. Long-term follow-up of patients with NAFLD and elevated liver enzymes. Hepatology 2006; 44:865-873.
8. Gupta A K, Bray G A, Greenway F L, Martin C K, Johnson W D, Smith S R. Pioglitazone, but not metformin, reduces liver fat in Type-2 diabetes mellitus independent of weight changes. J Diabetes Complications 2009.
9. Sanyal A J, Chalasani N, Kowdley K V et al. Pioglitazone, vitamin E, or placebo for nonalcoholic steatohepatitis. N Engl J Med 2010; 362:1675-1685.
10. Duvnjak M, Tomasic V, Gomercic M, Smircic Duvnjak L Barsic N, Lerotic I, Therapy of nonalcoholic fatty liver disease: current status, J Physiol Pharmacol 2009; 60 Suppl 7:57-66, 11. Mishra P, Younossi Z M. Current treatment strategies for non-alcoholic fatty liver disease (NAFLD). Curr Drug Discov Technol 2007:4:133-140.
12. Rogers P M M N. Rathod M A, Dubuisson O, Wang Z Q, Dasuri K, Babin S, Gupta A, Markward N, Cefalu W T, Dhurandhar N V. Metabolically Favorable Remodeling of Human Adipose Tissue by Human Adenovirus Ad-36 Diabetes 2008; 57:2321-2331.
13. Pasarica M, Mashtalir, N, McAllister, E J, Kilroy, G E, Koska, J. Permana. P, de Courten, B, Yu, M, Ravussin, E. Gimble, J M, Dhurandhar, N V. Adipogenic human adenovirus Ad-36 induces commitment, differentiation and lipid accumulation in human adipose-derived stem cells. Stem Cells 2008 26:969-978.
14 Nawrocki A R, Rajala M W, Tomas E et al. Mice lacking adiponectin show decreased hepatic insulin sensitivity and reduced responsiveness to peroxisome proliferator-activated receptor gamma agonists. J Biol Chem 2006; 281: 2654-2660.
15. Lutchman G, Promrat K, Kleiner D E et al. Changes in serum adipokine levels during pioglitazone treatment for nonalcoholic steatohepatitis: relationship to histological improvement. Clin Gastroenterol Hepatol 2006; 4:1048-1052.
16. Shen Z. Liang X, Rogers C Q, Rideout D, You M. Involvement of adiponectin-SIRT1-AMPK signaling in the protective action of rosiglitazone against alcoholic fatty liver in mice. Am J Physiol Gastrointest Liver Physiol 2010; 298:G364-374.
17. Habib Z A, Haystad S L, Wells K. Divine G, Pladevall M, Williams L K. Thiazolidinedione use and the longitudinal risk of fractures in patients with type 2 diabetes mellitus. J Clin Endocrinol Metab 2010; 95:592-600.
18. Ramos-Nino M E, MacLean C D, Littenberg B. Association between cancer prevalence and use of thiazolidinediones: results from the Vermont Diabetes Information System. BMC Med 2007; 5:17.
19. Lipscombe L L, Gomes T, Levesque L E, Flux J E, Juurlink D N, Alter D A. Thiazolidinediones and cardiovascular outcomes in older patients with diabetes. JAMA 2007; 298; 2634-2643.
20. Fernandes-Santos C, Evangelista Carneiro R, de Souza Mendonca L, Barbosa Aguila M, Mandarim-de-Lacerda C A. Rosiglitazone aggravates nonalcoholic Fatty pancreatic disease in C57BL/6 mice fed high-fat and high-sucrose diet. Pancreas 2009; 38:e80-86.
21. Fernandes-Santos C, Carneiro R E, de Souza Mendonca L, Aguila M B, Mandarim-de-Lacerda C A. Pan-PPAR agonist beneficial effects in overweight mice fed a high-fat high-sucrose diet. Nutrition 2009:25:818-827.
22. Todd M K, Watt M J, Le J, Hevener A L, Turcotte L P. Thiazolidinediones enhance skeletal muscle triacylglycerol synthesis while protecting against fatty acid-induced inflammation and insulin resistance, Am J Physiol Endocrinol Metab 2007; 292:E485-493.
23. Kuda O, Stankova B, Tvrzicka E et al. Prominent role of liver in elevated plasma palmitoleate levels in response to rosiglitazone in mice fed high-fat diet. J Physiol Pharmacol 2009; 60:135-140.
24. Trovato G M, Martines G F, Garozzo A et al. Ad36 adipogenic adenovirus in human non-alcoholic fatty liver disease. Liver Int 2009.
25. Mengshol J A, Golden-Mason L, Rosen H R. Mechanisms of Disease: HCV-induced liver injury. Nat Clin Pract Gastroenterol Hepatol 2007; 4:622-634.
26. Tsai W L, Chung R T. Viral hepatocarcinogenesis. Oncogene 2010; 29:2309-2324.
27. Hanlon G W. Bacteriophages: an appraisal of their role in the treatment of bacterial infections. Int J Antimicrob Agents 2007; 30:118-128.
28. Bischoff J R, Kim D H, Williams A et al. An adenovirus mutant that replicates selectively in p53-deficient human tumor cells. Science 1996; 274:373-376.
29. Crompton A M, Kim D H. From ONYX-015 to armed vaccinia viruses: the education and evolution of oncolytic virus development. Curr Cancer Drug Targets 2007; 7:133-139.
30. Pan Q, Liu B, Liu J, Cai R, Wang Y, Qian C. Synergistic induction of tumor cell death by combining cisplatin with an oncolytic adenovirus carrying TRAIL. Mol Cell Biochem 2007.
31. Libertini S, Iacuzzo I, Ferraro A et al. Lovastatin Enhances the Replication of the Oncolytic Adenovirus dl1520 and its Antineoplastic Activity Against Anaplastic Thyroid Carcinoma Cells. Endocrinology 2007.
32. Heiker J T, Kosel D, Beck-Sickinger A G. Molecular advances of adiponectin and adiponectin receptors. Biol Chem 2010.
33. Kim J Y, van de Wall E. Laplante M et al. Obesity-associated improvements in metabolic profile through expansion of adipose tissue. J Clin Invest 2007; 117:2621-2637.
34. Xu A. Wang Y, Keshaw H, Xu L Y, Lam K S, Cooper G J. The fat-derived hormone adiponectin alleviates alcoholic and nonalcoholic fatty liver diseases in mice. J Clin Invest 2003; 112:91-100.
35. Vitola B E, Deivanayagam S, Stein R1, Mohammed B S, Magkos F, Kirk E P, et al. Weight loss reduces liver fat and improves hepatic and skeletal muscle insulin sensitivity in obese adolescents. Obesity (Silver Spring) 2009; 17: 1744-1748.
36. Wang Z Q C W. Zhang X H, Yongmei Y. Qin J, Son L, Rogers P M, Mashtalir N, Bordelon J R, Ye J, Dhurandhar N V. Human adenovirus type 36 enhances glucose uptake in diabetic and non-diabetic human skeletal muscle cells independent of insulin signaling. Diabetes 2008; 57 1805-1813.
37. Pasarica M, Shin A C, Yu M, Ou Yang H M, Rathod M, Jen K L, et al. Human adenovirus 36 induces adiposity, increases insulin sensitivity, and alters hypothalamic monoamines in rats. Obesity (Silver Spring) 2006; 14: 1905-1913.
38. Kantartzis K, Schick F, Haring H U, Stefan N. Environmental and genetic determinants of fatty liver in humans. Dig Dis 2010; 28: 169-178.
39. Magkos F, Fabbrini E, Mohammed B S, Patterson B W, Klein S. Increased Whole-Body Adiposity Without a Concomitant Increase in Liver Fat is Not Associated With Augmented Metabolic Dysfunction. Obesity (Silver Spring) 2010.
40. Foy H M, Grayston J T. Adenoviruses. "Viral infections of humans: Epidemiology and control". Evans Alfred S. Ed. Plenum Medical: New York, 1976, pp 53-70.
41. Horvath J, Palkonyay L, Weber J. Group C adenovirus DNA sequences in human lymphoid cells. J Virol 1986; 59: 189-192.
42. Hierholzer J C, Wigand R, Anderson L J, Adrian T, Gold J W. Adenoviruses from patients with AIDS: a plethora of serotypes and a description of five new serotypes of subgenus D (types 43-47). J Infect Dis 1988; 158: 804-813.
43. Wigand R, Gelderblom H, Wadell G. New human adenovirus (candidate adenovirus 36), a novel member of subgroup D. Arch Virol 1980; 64: 225-233.

44. Dhurandhar N V, Israel B A, Kolesar J M, Mayhew G, Cook M E, Atkinson R L. Transmissibility of adenovirus-induced adiposity in a chicken model. Int J Obes Relat Metab Disord 2001; 25: 990-996.
45. Dhurandhar N V, Israel B A, Kolesar J M, Mayhew G F, Cook M E, Atkinson R L. Increased adiposity in animals due to a human virus. Int J Obes Relat Metab Disord 2000: 24: 989-996.
46. Dhurandhar N V, Whigham L D, Abbott D H, Schultz-Darken N J, Israel B A, Bradley S M, et al. Human adenovirus Ad-36 promotes weight in male rhesus and marmoset monkeys. J Nutr 2002; 132: 3155-3160.
47. Pasarica M, Loiler S, Dhurandhar N V. Acute effect of infection by adipogenic human adenovirus Ad36. Archives of Virology 2008; 153 (11): 2097-2102,
48. Atkinson R, Dhurandhar N, Allison D. Bower R, Israel B. Evidence for an association of an obesity virus with human obesity at three sites in the United States. Int J Obes 1998; 22: S57.
49. Bouchard C, Leon A S, Rao D C, Skinner J S, Wilmore H, Gagnon J. The HERITAGE family study. Aims, design, and measurement protocol. Med Sci Sports Exerc 1995; 27: 721-729.
50. Tompkins C L, Cefalu W, Ravussin E, Goran M, Soros A, Volaufova J, et al. Feasibility of ntravenous glucose tolerance testing prior to puberty. Int J Pediatr Obes 2010; 5: 51-55.
51. Larson-Meyer D E, Newcomer B R, VanVrancken-Tompkins C L, Sothern M. Feasibility of assessing liver lipid by proton magnetic resonance spectroscopy in healthy normal and overweight prepubertal children. Diabetes Technol Ther 2010; 12: 207-212.
52. Butte N F, Cai G, Cole S A, Wilson T A, Fisher J O, Zakeri I F, et al. Metabolic and behavioral predictors of weight gain in Hispanic children: the Viva la Familia Study. Am J Clin Nutr 2007; 85: 1478-1485.
53. Yamauchi T, Kamon J, Minokoshi Y, Ito Y, Waki H, Uchida S, et al. Adiponectin stimulates glucose utilization and fatty-acid oxidation by activating AMP-activated protein kinase. Nat Med 2002; 8: 1288-1295.
54. You M, Considine R V, Leone T C, Kelly D P, Crabb D W. Role of adiponectin in the protective action of dietary saturated fat against alcoholic fatty liver in mice. Hepatology 2005; 42: 568-577.
55. Pajvani U B, Scherer P E. Adiponectin: systemic contributor to insulin sensitivity. Curr Diab Rep 2003; 3: 207-213.
56. Waki H. Yamauchi T, Kamon J, Ito Y, Uchida S, Kita S, et al. Impaired multimerization of human adiponectin mutants associated with diabetes. Molecular structure and multimer formation of adiponectin. J Biol Chem 2003; 278: 40352-40363.
57. Schraw T, Wang Z V, Halberg N, Hawkins M, Scherer P E. Plasma adiponectin complexes have distinct biochemical characteristics. Endocrinology 2008; 149: 2270-2282.
58. Zhang W, Patil S, Chauhan B, Guo S, Powell D R, Le J, et al. FoxO1 regulates multiple metabolic pathways in the liver: effects on gluconeogenic, glycolytic, and lipogenic gene expression. J Biol Chem 2006; 281: 10105-10117.
59. Yoon M. The role of PPARalpha in lipid metabolism and obesity: focusing on the effects of estrogen on PPARalpha actions. Pharmacol Res 2009; 60: 151-159.
60. Louet J F, Le May C, Pegorier J P, Decaux J F, Girard J. Regulation of liver carnitine palmitoyltransferase I gene expression by hormones and fatty acids. Biochem Soc Trans 2001:29:310-316.
61. Kotokorpi P, Ellis E, Parini P, Nilsson L M, Strom S, Steffensen K R, et al. Physiological differences between human and rat primary hepatocytes in response to liver X receptor activation by 3-[3-[N-(2-chloro-3-trifluoromethylbenzyl)-(2,2-diphenylethyl)amino]propyl oxy]phenylacetic acid hydrochloride (GW3965). Mol Pharmacol 2007:72:947-955.
62. Liao W, Kobayashi K, Chan L. Adenovirus-mediated overexpression of microsomal triglyceride transfer protein (MTP): mechanistic studies on the role of MTP in apolipoprotein B-100 biogenesis, by, Biochemistry 1999; 38: 10215.
63. Liao W, Kobayashi K, Chan L. Adenovirus-mediated overexpression of microsomal triglyceride transfer protein (MTP): mechanistic studies on the role of MTP in apolipoprotein B-100 biogenesis. Biochemistry 1999; 38: 7532-7544.
64. Tietge U J, Bakillah A, Maugeais C, Tsukamoto K, Hussain M, Rader D J. Hepatic overexpression of microsomal triglyceride transfer protein (MTP) results in increased in vivo secretion of VLDL triglycerides and apolipoprotein B. J Lipid Res 1999; 40: 2134-2139.
65. Dixon J L, Ginsberg H N. Regulation of hepatic secretion of apolipoprotein B-containing lipoproteins: information obtained from cultured liver cells. J Lipid Res 1993; 34: 167-179.
66. Davidson N O, Shelness G S. APOLIPOPROTEIN B: mRNA editing, lipoprotein assembly, and presecretory degradation. Annu Rev Nutr 2000; 20: 169-193.
67. Polyzos S A, Kountouras J, Zavos C, Tsiaousi E. The role of adiponectin in the pathogenesis and treatment of nonalcoholic fatty liver disease. Diabetes Obes Metab 2010; 12: 365-383.
68. Gao Z, Yin J, Zhang J. He Q. McGuinness O P, Ye J. Inactivation of NF-kappaB p50 leads to insulin sensitization in liver through post-translational inhibition of p70S6K. J Biol Chem 2009:284:18368-18376.
69. Xu F. Gao Z, Zhang J, Rivera C A, Yin J, Weng J. et al. Lack of SIRT1 (Mammalian Sirtuin 1) activity leads to liver steatosis in the SIRT1+/− mice: a role of lipid mobilization and inflammation. Endocrinology 2010; 151: 2504-2514.
70. Vangipuram S D, Sheele J. Atkinson R L, Holland T C, Dhurandhar N V. A human adenovirus enhances preadipocyte differentiation. Obes Res 2004; 12: 770-777.
71. Gao Z. Wang Z. Zhang X. Butler A A, Zuberi A, Gawronska-Kozak B, et al. Inactivation of PKCtheta leads to increased susceptibility to obesity and dietary insulin resistance in mice. Am J Physiol Endocrinol Metab 2007; 292: E84-91.
72. Cefalu W T, Wang Z Q, Bell-Farrow A, Ralapati S. Liver and kidney tissue membranes as tissue markers for nonenzymatic glycosylation. Diabetes 1991; 40: 902-907.
73. Lupo M A. Cefalu W I, Pardridge W M. Kinetics of lactate transport into rat liver in vivo. Metabolism 1990; 39: 374-377.
74. Hillyard L A, Lin C Y, Abraham S. Lipogenic enzyme activities in primary cultures of adult mouse hepatocytes. Lipids 1988; 23: 242-247.
75. Amatruda J M, Danahy S A, Chang C L. The effects of glucocorticoids on insulin-stimulated lipogenesis in primary cultures of rat hepatocytes. Biochem J 1983; 212: 135-141.
76. C. W. Wang Z Q, Zhang X H, Yongmei Y, Qin J, Son L, Rogers P M, Mashtalir N, Bordelon J R, Ye J, Dhurandhar N V., Diabetes 57 1805 (2008).
77. G. Sesti. M. Federici, D. Lauro, P. Sbraccia, R. Lauro, Diabetes Metab Res Rev 17, 363 (September-October, 2001).

78. G. Sesti et al., FASEB J 15, 2099 (October, 2001).
79. R. K. Semple et al., Diabetes Care 31, 977 (May, 2008).
80. R. K. Semple et al., J Clin Invest 119, 315 (February, 2009).
81. J. E. Pessin, A. R. Saltiel, J Clin Invest 106, 165 (July, 2000).
82. L. J. Goodyear et al., J Clin Invest 95, 2195 (May, 1995).
83. M. J. Pagliassotti, J. Kang, J. S. Thresher, C. K. Sung, M. E. Bizeau, Am J Physiol Endocrinol Metab 282, E170 (January, 2002).
84. N. G. Boule et al., Diabetes Care 28, 108 (January, 2005).
85. N. F. Butte, G. Cai, S. A. Cole, A. G. Comuzzie, Am J Clin Nutr 84, 646 September, 2006).
86. C. C. Cowie et al. Diabetes Care 32, 287 (February, 2009).
87. G. Zhou et al., J Clin Invest 108, 1167 (October, 2001).
88. G. D. Cartee, J. F. Wojtaszewski, Appl Physiol Nutr Metab 32, 557 (June, 2007).
89. Z. Gao et al., J Biol Chem 277, 48115 (Dec. 13, 2002).
90. E. Maury, S. M. Brichard, Mol Cell Endocrinol 314, 1 (January 15).
91. M. Qatanani, M. A. Lazar, Genes Dev 21, 1443 (Jun. 15, 2007).
92. R. L. Atkinson et al. Int J Obes (Lond) 29, 281 (March, 2005).
93. P. An et al., Metabolism 52, 246 (February, 2003).
94. R. C. Boston et al., Diabetes Technol Ther 5, 1003 (2003).
95. S. Bajpeyi et al., J Appl Physiol 106, 1079 (April, 2009).
96. F. Aoki et al., Biosci Biotechnol Biochem 71, 206 (January, 2007).
97. A. Raben, N. Haulrik, N. Dhurandhar, R. Atkinson, A. Astrup, Int J Obes 25 (Suppl 2), S46 (2001).

The invention claimed is:

1. A method of treating or preventing non-alcoholic fatty liver disease in an individual, said method comprising administering to the patient a therapeutically effective amount of Adenovirus-36 E4orf1 protein, wherein said protein is SEQ ID NO: 2, SEQ ID NO:4 or functional variant thereof, wherein said functional variant has at least 85% sequence identity to SEQ ID NO:2 or SEQ ID NO:4, or a nucleic acid encoding Adenovirus-36 E4orf1, wherein said nucleic acid is SEQ ID NO:1 or SEQ ID NO:3 or functional variant thereof, wherein said functional variant has at least 85% sequence identity to SEQ ID NO:1 or SEQ ID NO:4, or an analog of Adenovirus-36 E4orf1, wherein the patient's symptoms improve following said administration.

2. The method of claim 1, wherein an Adenovirus-36 E4orf1 protein is administered and the amino acid sequence of the Adenovirus-36 E4orf1 protein is SEQ ID NO:2 or a functional variant thereof, wherein said functional variant has at least 85% sequence identity to SEQ ID NO:2.

3. The method of claim 1, wherein a nucleic acid encoding Adenovirus-36 E4orf1 protein is administered by introducing into the mammal a nucleic acid sequence encoding the Adenovirus-36 E4orf1 protein, in a manner permitting expression of the Adenovirus-36 E4orf1 protein.

4. The method of claim 3, wherein the nucleic acid sequence is introduced by a method selected from the group consisting of electroporation, DEAE Dextran transfection, calcium phosphate transfection, cationic liposome fusion, proptoplast fusion, creation of an in vivo electric tield, DNA-coated microprojectile bombardment, injection with recombinant replication-defective viruses, homologous recombination, in vivo gene therapy, ex vivo gene therapy, viral vectors, and naked DNA transfer.

5. The method of claim 3, wherein the nucleic acid sequence comprises SEQ ID NO:1 or a functional variant thereof, wherein said functional variant has at least 85% sequence identity to SEQ ID NO:1.

6. The method of claim 1, wherein said individual is a human.

7. A method of reducing excessive fat from the liver in an individual, said method comprising administering to the patient a therapeutically effective amount of Adenovirus-36 E4 orf1 protein or functional variant thereof, wherein said protein is SEQ ID NO:2 or SEQ ID NO:4, or a functional variant having at least 85% sequence identity to SEQ ID NO:2 or SEQ ID NO:4, and wherein the fat in the liver is lowered following said administration.

8. The method of claim 7, wherein the amino acid sequence of the Adenovirus-36 E4orf1 protein is SEQ ID NO:2 or functional variant thereof, wherein said functional variant has at least 85% sequence identity to SEQ ID NO:2.

9. The method of claim 7, wherein the Adenovirus-36 E4orf1 protein is administered by introducing into the mammal a nucleic acid sequence encoding the Adenovirus-36 E4orf1 protein, in a manner permitting expression of the Adenovirus-36 E4orf1 protein.

10. The method of claim 9, wherein the nucleic acid sequence is introduced by a method selected from the group consisting of electroporation, DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, vivo gene therapy, ex vivo gene therapy, viral vectors, and naked DNA transfer.

11. The method of claim 9, wherein the nucleic acid sequence comprises SEQ ID NO:1 or functional variant thereof, wherein said functional variant has at least 85% sequence identity to SEQ ID NO:1.

12. The method of claim 7, wherein said individual is a human.

13. A method of treating or preventing liver dysfunction, characterized by fatty liver and insulin resistance, said method comprising administering to said patient a therapeutically effective amount of Ad36 E4orf1 protein or functional variant thereof, wherein said protein is SEQ ID NO:2, SEQ ID NO:4 or a functional variant having at least 85% sequence identity to SEQ ID NO:2 or SEQ ID NO:4, and wherein liver fat accumulation is improved following said administration.

14. The method of claim 13, wherein said liver fat accumulation improvement is characterized by increased lipid oxidation or increase transport of lipid from the liver.

15. The method of claim 13, wherein an Adenovirus-36 E4orf1 protein is administered and the amino acid sequence of the Adenovirus-36 E4 orf1 protein is SEQ ID NO:2 or functional variant thereof, wherein said functional variant has at least 85% sequence identity to SEQ ID NO:2.

16. The method of claim 13, wherein a nucleic acid encoding Adenovirus-36 E4orf1 protein is administered by introducing into the mammal a nucleic acid sequence encoding the Adenovirus-36 E4orf1 protein, in a manner permitting expression of the Adenovirus-36 E4orf1 protein.

17. The method of claim 16, wherein the nucleic acid sequence is introduced by a method selected from the group consisting of electroporation, DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, viral vectors, and naked DNA transfer.

18. The method of claim 16, wherein the nucleic acid sequence comprises SEQ ID NO:1 or functional variant thereof, wherein said functional variant has at least 85% sequence identity to SEQ NO:1.

19. The method of claim 13, wherein said individually is a human.

20. A method of reducing or preventing non-alcoholic steato-hepatitis (NASH), said method comprising administering to said patient a therapeutically effective amount of Ad36 E4orf1 protein or functional variant thereof, wherein said protein is SEQ ID NO:2, SEQ ID NO:4 or a functional variant having at least 85% sequence identity to SEQ ID NO:2 or SEQ ID NO:4, wherein the occurrence of NASH is reduced or prevented.

21. The method of claim 20, wherein hyperglycemia resulting from hepatic dysfunction is reduced in the individual.

22. The method of claim 20, wherein an Adenovirus-36 E4orf1 protein is administered and the amino acid sequence of the Adenovirus-36 E4 orf1 protein is SEQ ID NO:2 or functional variant thereof, wherein said functional variant has at least 85% sequence identity to SEQ ID NO:2.

23. The method of claim 20 wherein a nucleic acid encoding Adenovirus-36 E4orf1 protein is administered by introducing into the mammal a nucleic acid sequence encoding the Adenovirus-36 E4orf1 protein, in a manner permitting expression of the Adenovirus-36 E4orf1 protein.

24. The method of claim 22, wherein the nucleic acid sequence is introduced by a method selected from the group consisting of electroporation, DEAL Dextran transfection, calcium phosphate transfection, cationic liposome fusion, proptoplast fusion, creation of an in vivo electric field, DNA-coated microprojectile bombardment injection with recombinant replication-defective viruses, homologous recombination, in vivo gene therapy, ex vivo gene therapy, viral vectors, and naked DNA transfer.

25. The method of claim 22, wherein the nucleic acid sequence comprises SEQ ID NO:1 or functional variant thereof, wherein said functional variant has at least 85% sequence identity to SEQ ID NO:1.

26. The method of claim 20, wherein said individual is a human.

* * * * *

SEQUENCE LISTING

```
<160> NUMBER OF SEQ ID NOS: 10

<210> SEQ ID NO 1
<211> LENGTH: 378
<212> TYPE: DNA
<213> ORGANISM: Human adenovirus 36

<400> SEQUENCE: 1
atggctgaat ctctgtatgc tttcatagat agccctggag ggatcgctcc cgtccaggaa      60
ggggctagca atagatatat cttcttttgc cccgaatctt tccacattcc tccgcatggg     120
gtgatattgc ttcacctcag agtgagcgtg ctggttccta ctggatatca gggcagattt     180
atggccttga atgactacca tgccaggggc atactaaccc agtccgatgt gatatttgcc     240
gggagaagac atgatctctc tgtgctgctc tttaaccaca cggaccgatt tttgtatgtc     300
cgcgagggcc acccagtggg aaccctgctg ctggagagag tgattttcc ttcagtgaga     360 atagccaccc tggtttag                                                   378

<210> SEQ ID NO 2
<211> LENGTH: 125
<212> TYPE: PRT
<213> ORGANISM: Human adenovirus 36

<400> SEQUENCE: 2

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
                20                  25                  30

Ser Phe His Ile Pro Pro His Gly Val Ile Leu Leu His Leu Arg Val
            35                  40                  45

Ser Val Leu Val Pro Thr Gly Tyr Gln Gly Arg Phe Met Ala Leu Asn
        50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
                85                  90                  95

Phe Leu Tyr Val Arg Glu Gly His Pro Val Gly Thr Leu Leu Leu Glu
                100                 105                 110

Arg Val Ile Phe Pro Ser Val Arg Ile Ala Thr Leu Val
            115                 120                 125

<210> SEQ ID NO 3
```

```
<211> LENGTH: 366
<212> TYPE: DNA
<213> ORGANISM: Human adenovirus 36

<400> SEQUENCE: 3
atggctgaat ctctgtatgc tttcatagat agccctggag ggatcgctcc cgtccaggaa      60
ggggctagca atagatatat cttcttttgc cccgaatctt tccacattcc tccgcatggg     120
gtgatattgc ttcacctcag agtgagcgtg ctggttccta ctggatatca gggcagattt     180
atggccttga tgactacca tgccagggc atactaaccc agtccgatgt gatatttgcc      240
gggagaagac atgatctctc tgtgctgctc tttaaccaca cggaccgatt tttgtatgtc     300
cgcgagggcc acccagtggg aaccctgctg ctggagagag tgattttttcc ttcagtgaga     360 atatag                                                                 366

<210> SEQ ID NO 4
<211> LENGTH: 121
<212> TYPE: PRT
<213> ORGANISM: Human adenovirus 36

<400> SEQUENCE: 4

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
                20                  25                  30

Ser Phe His Ile Pro Pro His Gly Val Ile Leu Leu His Leu Arg Val
            35                  40                  45

Ser Val Leu Val Pro Thr Gly Tyr Gln Gly Arg Phe Met Ala Leu Asn
        50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
                85                  90                  95

Phe Leu Tyr Val Arg Glu Gly His Pro Val Gly Thr Leu Leu Leu Glu
            100                 105                 110

Arg Val Ile Phe Pro Ser Val Arg Ile
        115                 120

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcatactaa cccagtccga tg                                                22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcactctcag cagcagcagg                                                   20
```

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctaggcagg agggtttttc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atagcccggg ggaatacata                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatcttcatg gtgctaggag                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgttgacat ccgtaaagac                                              20
```